United States Patent
Kinoshita et al.

(10) Patent No.: US 8,608,671 B2
(45) Date of Patent: Dec. 17, 2013

(54) GAIT CHANGE DETERMINATION DEVICE

(75) Inventors: Shigeo Kinoshita, Dalian (CN);
Kentaro Mori, Nagaokakyo (JP);
Tetsuya Sato, Nishinomiya (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/812,362

(22) PCT Filed: Jul. 19, 2011

(86) PCT No.: PCT/JP2011/066339
§ 371 (c)(1),
(2), (4) Date: Jan. 25, 2013

(87) PCT Pub. No.: WO2012/014714
PCT Pub. Date: Feb. 2, 2012

(65) Prior Publication Data
US 2013/0123669 A1    May 16, 2013

(30) Foreign Application Priority Data

Jul. 27, 2010    (JP) ................................ 2010-167932

(51) Int. Cl.
*A61B 5/117*    (2006.01)
*A61B 5/103*    (2006.01)

(52) U.S. Cl.
USPC ....................................................... 600/595

(58) Field of Classification Search
USPC ............................................... 600/587, 595
See application file for complete search history.

(56) References Cited

U.S. PATENT DOCUMENTS

2012/0209149 A1    8/2012    Yoneyama et al.

FOREIGN PATENT DOCUMENTS

| JP | 2002-165799 A | 6/2002 |
| JP | 2003-102693 A | 4/2003 |
| JP | 2006-177749 A | 7/2006 |
| JP | 2006-271893 A | 10/2006 |
| JP | 2009-106386 A | 5/2009 |
| JP | 2009-125508 A | 6/2009 |
| WO | 2011/040259 A1 | 4/2011 |

OTHER PUBLICATIONS

Official Communication issued in International Patent Application No. PCT/JP2011/066339, mailed on Aug. 16, 2011.

*Primary Examiner* — Brian Szmal
(74) *Attorney, Agent, or Firm* — Keating & Bennett, LLP

(57) ABSTRACT

A gait change determination device includes a main body unit, an accelerometer that detects an acceleration of the main body unit, and a control unit, and determines a change in the gait of a user that wears the main body unit on a predetermined area. The control unit specifies a trajectory of a predetermined area on which the main body unit is worn during walking based on accelerations detected by the accelerometer, calculates the temporal change amount of the specified trajectory, and determines the degree of change, which is the degree of the temporal change, based on the calculated temporal change. The degree of change in the gait can be more accurately determined.

8 Claims, 20 Drawing Sheets

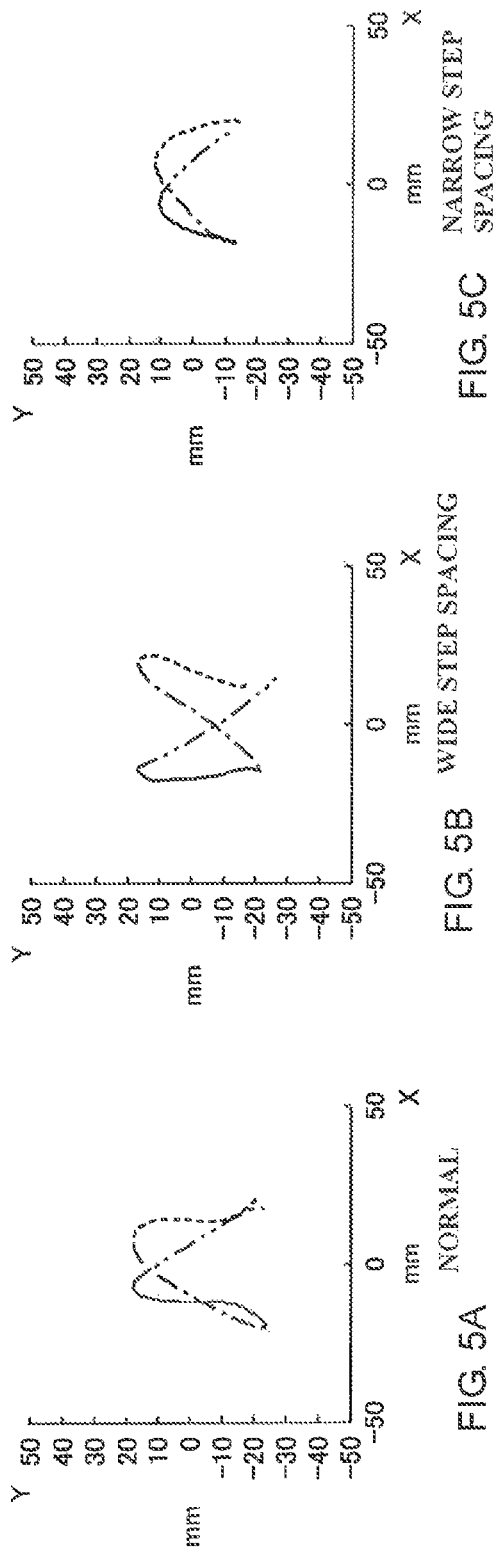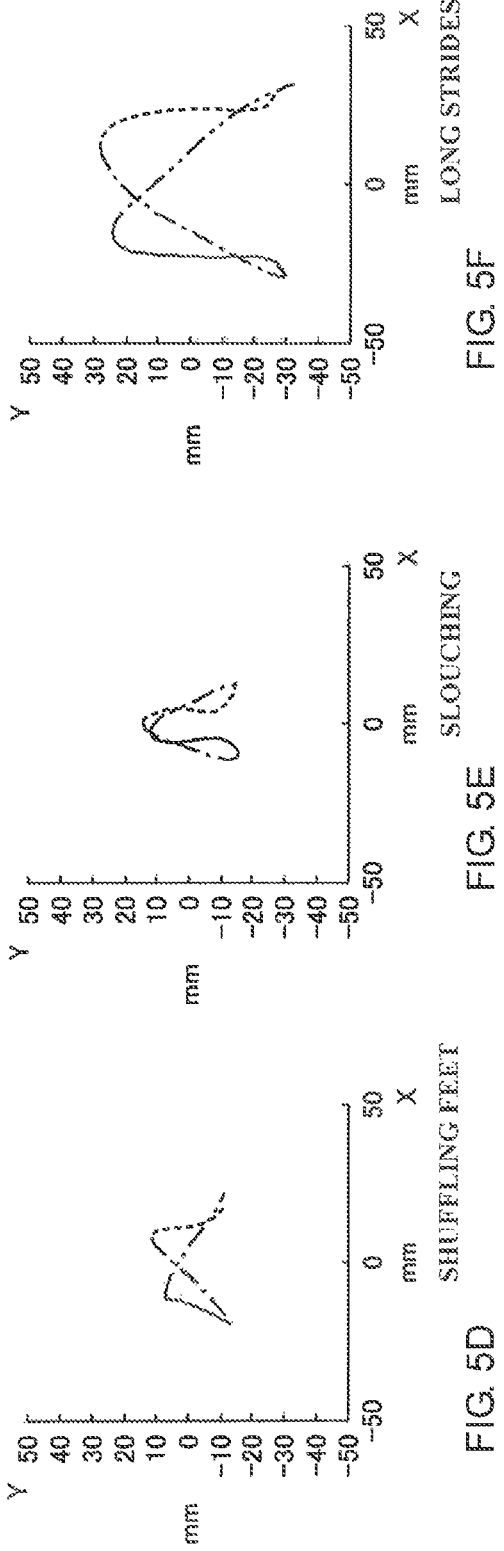

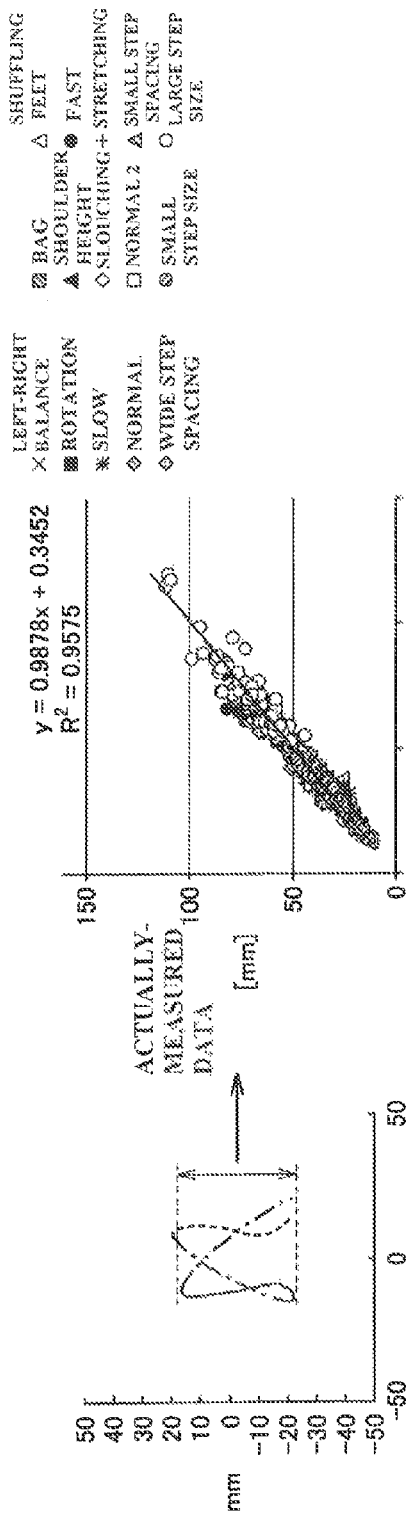
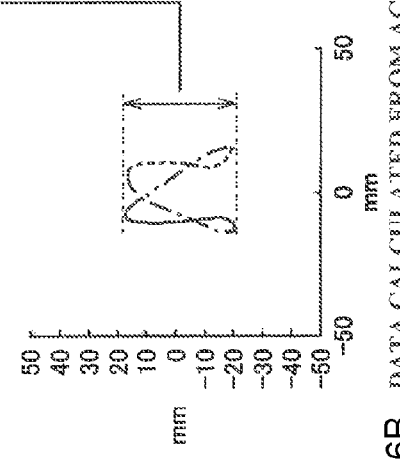
FIG. 6A ACTUALLY-MEASURED DATA
FIG. 6B DATA CALCULATED FROM ACCELERATION
FIG. 6C

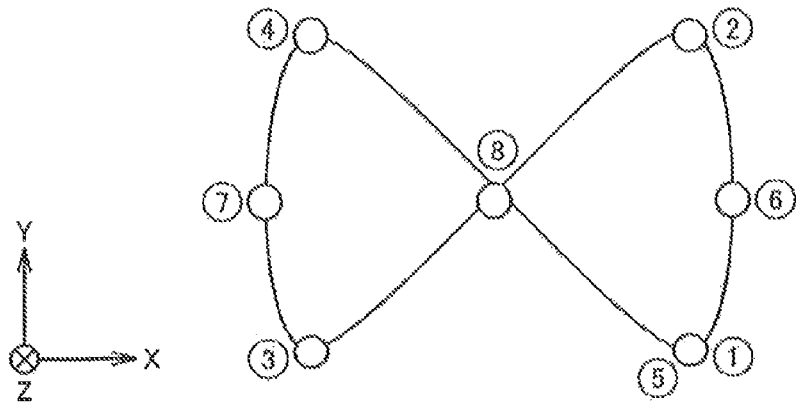

FIG.7A

| CHARACTERISTIC POINT NO. | GAIT CYCLE | CONDITIONS |
|---|---|---|
| 1 | RIGHT FOOT TOUCHING GROUND | HORIZONTAL = RIGHT AND VERTICAL = LOWERMOST |
| 2 | RIGHT FOOT STANDING STRAIGHT | VERTICAL = UPPERMOST AFTER NO. 1 |
| 3 | LEFT FOOT TOUCHING GROUND | VERTICAL = LOWERMOST AFTER NO. 2 |
| 4 | LEFT FOOT STANDING STRAIGHT | VERTICAL = UPPERMOST AFTER NO. 3 |
| 5 | RIGHT FOOT TOUCHING GROUND | VERTICAL = LOWERMOST AFTER NO. 4 *NO. 5 = NO. 1 IN NEXT CYCLE |
| 6 | FURTHEST RIGHT | MAXIMUM OF X ≥ 0 |
| 7 | FURTHEST LEFT | MINIMUM OF X < 0 |
| 8 | CROSS POINT | X OF STRAIGHT LINE 2 → 3 = X OF STRAIGHT LINE 4 → 5 OR X OF STRAIGHT LINE 1 → 2 = X OF STRAIGHT LINE 3 → 4 |

FIG.7B

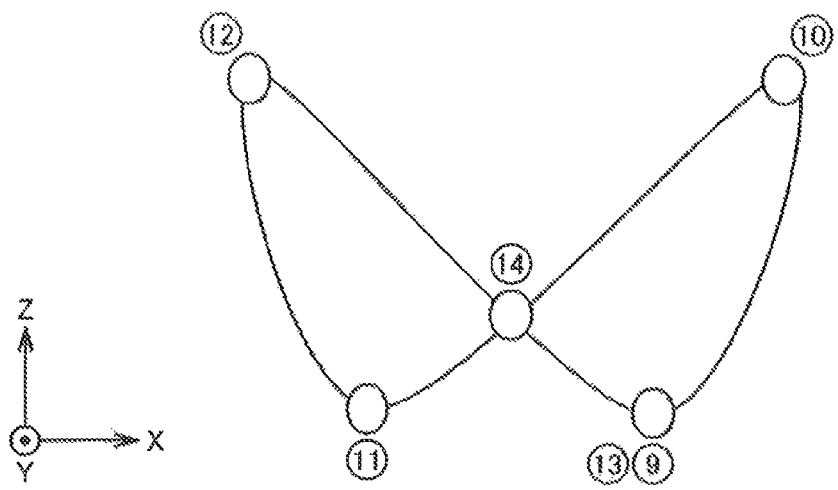

FIG.8A

| CHARACTERISTIC POINT NO. | GAIT CYCLE | CONDITIONS |
|---|---|---|
| 9 | RIGHT FOOT TOUCHING GROUND | HORIZONTAL = RIGHT AND DEPTH DIRECTION = REARMOST |
| 10 | RIGHT FOOT STANDING STRAIGHT | DEPTH DIRECTION = FORWARDMOST AFTER NO. 9 |
| 11 | LEFT FOOT TOUCHING GROUND | DEPTH DIRECTION = REARMOST AFTER NO. 10 |
| 12 | LEFT FOOT STANDING STRAIGHT | DEPTH DIRECTION = FORWARDMOST AFTER NO. 11 |
| 13 | RIGHT FOOT TOUCHING GROUND | DEPTH DIRECTION = REARMOST AFTER NO. 12 |
| 14 | CROSS POINT | |

FIG.8B

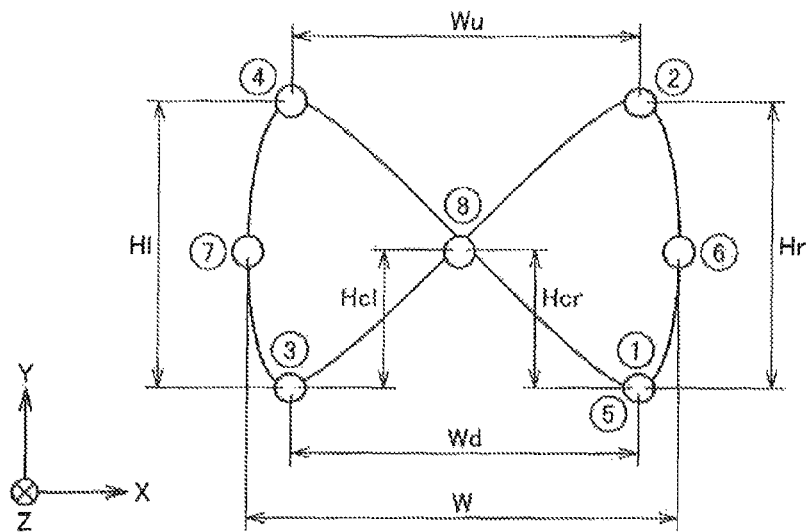

FIG. 10A

| CHARACTERISTIC FACTOR | DEFINITION | FORMULA |
|---|---|---|
| Wu | UPPER-SIDE HORIZONTAL WIDTH | X2−X4 |
| Wd | LOWER-SIDE HORIZONTAL WIDTH | X1−X3 |
| W | HORIZONTAL WIDTH | X6−X7 |
| Hl | LEFT-SIDE VERTICAL WIDTH | Y4−Y3 |
| Hr | RIGHT-SIDE VERTICAL WIDTH | Y2−Y1 |
| H | VERTICAL WIDTH | (Hl+Hr)/2 |
| Hcl | LEFT-SIDE CROSS POINT HEIGHT | Y8−Y3 |
| Hcr | RIGHT-SIDE CROSS POINT HEIGHT | Y8−Y1 |
| ISO | PHASE | ((Hcl/Hl)+(Hcr/Hr))/2 |
| Vlev | SHAPE V OR ∧ | Wu/Wd |
| Ilev | SHAPE I | H/W |
| Hb | RIGHT/LEFT VERTICAL WIDTH RATIO | Hr/Hl |
| Yb | LEFT/RIGHT HEIGHT RATIO | (Y4−Y1)/(Y2−Y3) |
| Wb | RIGHT/LEFT WIDTH RATIO | (X6−X8)/(X8−X7) |
| Stl | VERTICAL AMPLITUDE FROM RIGHT FOOT CONTACT TO LEFT FOOT CONTACT | (Y2−Y1)+(Y2−Y3) |
| Str | VERTICAL AMPLITUDE FROM LEFT FOOT CONTACT TO RIGHT FOOT CONTACT | (Y4−Y3)+(Y4−Y5) |
| jun | TRACE ORDER | X2>X4=CLOCKWISE DIRECTION |

FIG. 10B

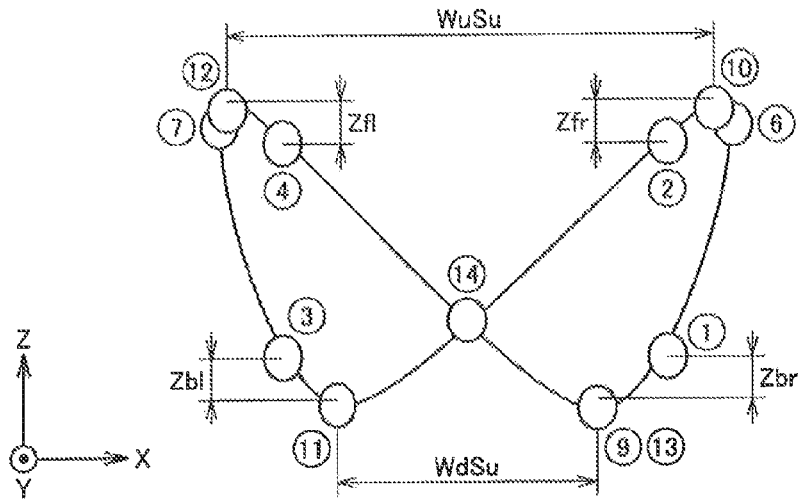

FIG. 11A

| CHARACTERISTIC FACTOR | DEFINITION | FORMULA |
|---|---|---|
| WuSu | UPPER-SIDE HORIZONTAL WIDTH | X10−X12 |
| WdSu | LOWER-SIDE HORIZONTAL WIDTH | X9−X11 |
| Wsu | HORIZONTAL WIDTH | X6−X7 |
| HlSu | LEFT-SIDE VERTICAL WIDTH | Z12−Z11 |
| HrSu | RIGHT-SIDE VERTICAL WIDTH | Z10−Z9 |
| Hsu | VERTICAL WIDTH | (HlSu+HrSu)/2 |
| HclSu | LEFT-SIDE CROSS POINT HEIGHT | Z8−Z11 |
| HcrSu | RIGHT-SIDE CROSS POINT HEIGHT | Z8−Z9 |
| ISOSu | PHASE | ISO |
| VlevSu | SHAPE V or Λ | WuSu/WdSu |
| IlevSu | SHAPE I | Hsu/Wsu |
| HbSu | RIGHT/LEFT VERTICAL WIDTH RATIO | HrSu/HlSu |
| YbSu | LEFT/RIGHT HEIGHT RATIO | (Z13−Z9)/(Z10−Z11) |
| WbSu | RIGHT/LEFT WIDTH RATIO | Wb |
| StlSu | DEPTH DIRECTION AMPLITUDE FROM RIGHT FOOT CONTACT TO LEFT FOOT CONTACT | (Z10−Z9)+(Z10−Z11) |
| StrSu | DEPTH DIRECTION AMPLITUDE FROM LEFT FOOT CONTACT TO RIGHT FOOT CONTACT | (Z12−Z11)+(Z12−Z13) |
| Zfl | WAIST DEPTH DIRECTION MOVEMENT FROM HIGHEST POINT WHEN STANDING ON LEFT FOOT | Z12−Z4 |
| Zfr | WAIST DEPTH DIRECTION MOVEMENT FROM HIGHEST POINT WHEN STANDING ON RIGHT FOOT | Z10−Z2 |
| Zf | WAIST DEPTH DIRECTION MOVEMENT FROM HIGHEST POINT WHEN STANDING ERECT | (Zfl+Zfr)/2 |
| Zbl | WAIST DEPTH DIRECTION MOVEMENT FROM LEFT FOOT CONTACT | Z11−Z3 |
| Zbr | WAIST DEPTH DIRECTION MOVEMENT FROM RIGHT FOOT CONTACT | Z9−Z5 |
| Zb | WAIST DEPTH DIRECTION MOVEMENT FROM GROUND CONTACT | (Zbl+Zbr)/2 |

FIG. 11B

| CHARACTERISTIC FACTOR | DEFINITION | FORMULA |
|---|---|---|
| dZ | DEPTH DIRECTION TILT | (Y2−Y1)/(Z2−Z1) |
| StlShi | LEFT DEPTH DIRECTION AMPLITUDE | (Z2,Y2)−(Z1,Y1)+(Z2,Y2)−(Z3,Y3) |
| StrShi | RIGHT DEPTH DIRECTION AMPLITUDE | (Z4,Y4)−(Z3,Y3)+(Z4,Y4)−(Z1,Y1) |
| StShi | DEPTH DIRECTION AMPLITUDE | (StlShi+StrShi)/2 |

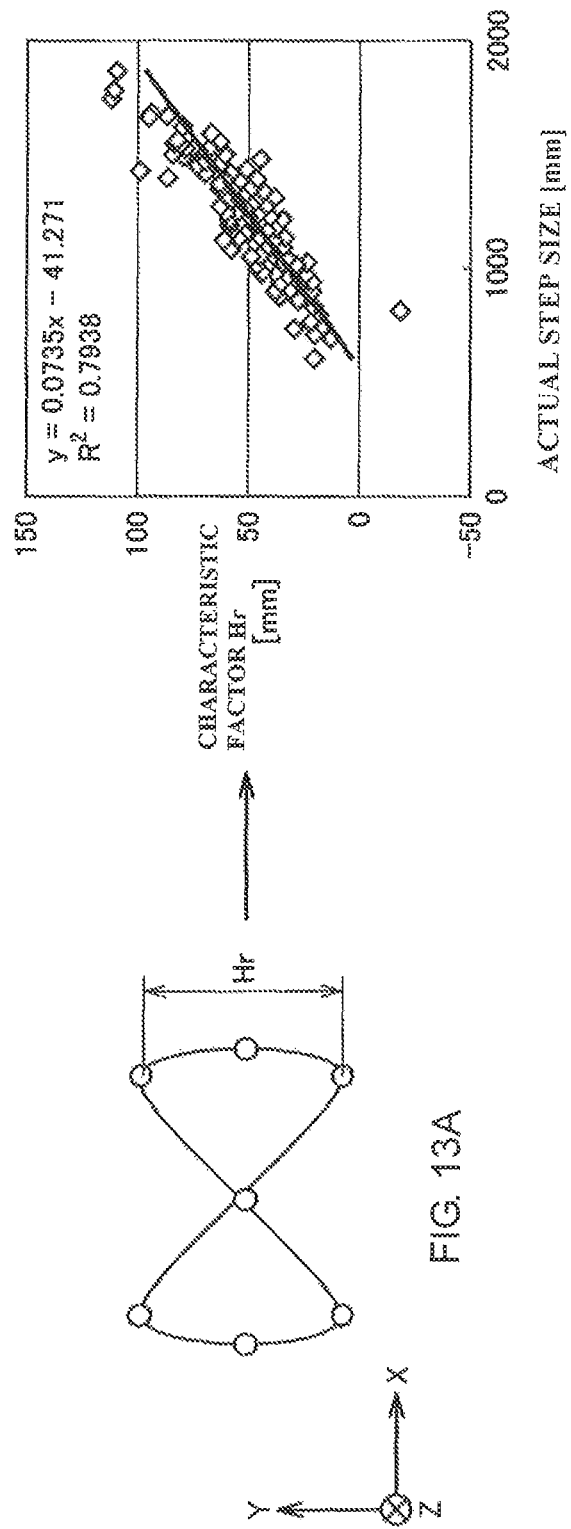

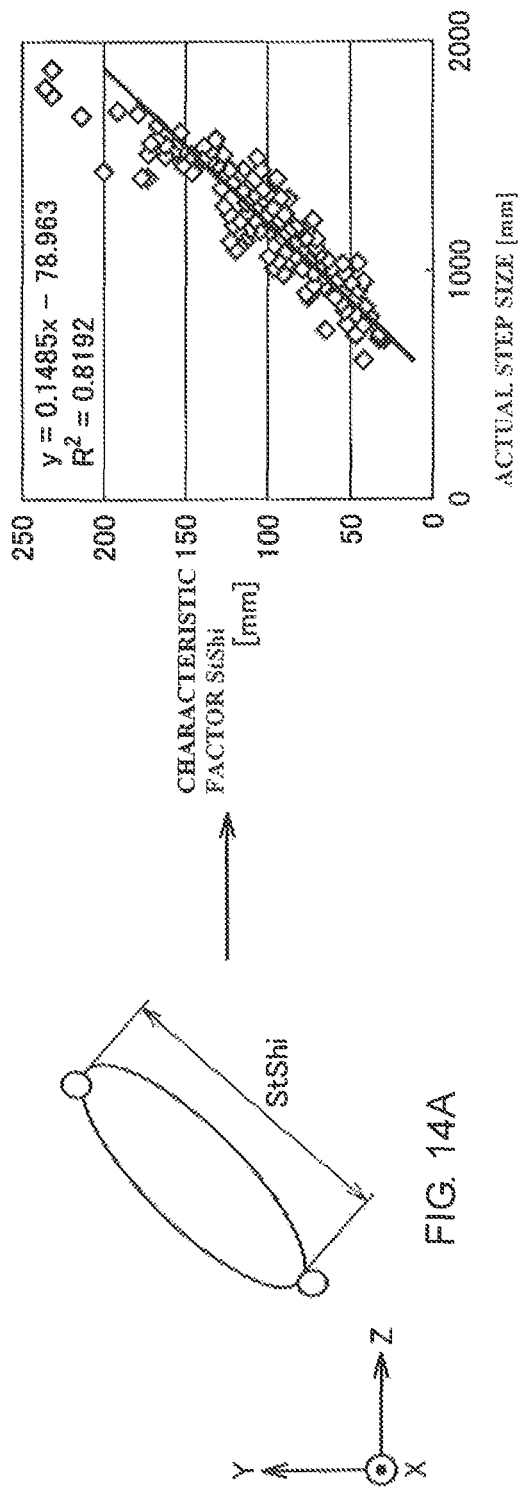

GAIT CHANGE DETERMINATION DEVICE

BACKGROUND OF THE INVENTION

1. Field of the Invention

The present invention relates to gait change determination devices, and particularly relates to gait change determination devices suited to determining a change in a walking state of a user wearing the device on a predetermined area.

2. Description of the Related Art

Thus far, there has been a technique that, based on values detected by an accelerometer, calculates a movement interval or the presence/absence of muscular vibrations (high-frequency acceleration components), and determines a level of fatigue based on the movement interval or the presence/absence of muscular vibrations (for example, see FIGS. 25 and 26 of JP 2006-271893A).

However, this conventional technique is problematic in that the technique is highly susceptible to the influence of the user simply changing his/her movement speed or the influence of differences among individual users. Accordingly, there has been a problem in that the degree of change in a gait cannot be accurately determined and communicated to the user.

SUMMARY OF THE INVENTION

Preferred embodiments of the present invention provide a gait change determination device capable of more accurately determining a degree of change in a gait.

A gait change determination device according to a preferred embodiment of the present invention includes a main body unit, an accelerometer that detects an acceleration of the main body unit, and a control unit, and determines a change in the gait of a user that wears the main body unit on a predetermined area.

The control unit preferably includes a specification unit that, based on the acceleration detected by the accelerometer, specifies a trajectory of the predetermined area on which the main body unit is worn during walking; a first calculation unit that calculates a temporal change in the trajectory specified by the specification unit; and a determination unit that, based on the temporal change calculated by the first calculation unit, determines a degree of change that is the degree of the temporal change.

Preferably, the gait change determination device further includes a storage unit. The control unit further includes an acceptance unit that accepts an input of a level of fatigue when the user is walking. The determination unit determines the degree of change when the degree of change has been accepted by the acceptance unit. The control unit further includes a storage control unit that stores the level of fatigue accepted by the acceptance unit and the degree of change determined by the determination unit in association with each other in the storage unit. The determination unit determines the level of fatigue that corresponds to the degree of change calculated by the determination unit based on the level of fatigue and the degree of change stored in the storage unit.

Preferably, the gait change determination device further includes an alert unit. The control unit further includes an alert control unit that communicates the level of fatigue determined by the determination unit using the alert unit.

Preferably, the trajectory is a three-dimensional trajectory from which has been removed a movement component in an advancement direction in which the predetermined area on which the main body unit is worn advances during walking, and a pattern of the trajectory includes multiple characteristic points that define characteristics of the pattern. The specification unit specifies positions of the characteristic points in the trajectory projected, with the movement component in the advancement direction removed, onto planes perpendicular or substantially perpendicular to each of three orthogonal axial directions, including a vertical direction, the advancement direction, and a horizontal direction, based on the acceleration calculated by the accelerometer. The first calculation unit preferably includes a second calculation unit that calculates values of characteristic factors of the trajectory based on the positions specified by the specification unit; a third calculation unit that, in accordance with a correlation relationship, determined in advance, between the values of the characteristic factors and the value of an index indicating the gait, calculates a value of the index, based on the values of the characteristic factors calculated by the second calculation unit; and a fourth calculation unit that calculates a temporal change amount of the index based on the value of the index calculated by the third calculation unit. The determination unit determines the degree of change based on the temporal change amount calculated by the fourth calculation unit.

Further preferably, the temporal change amount includes a temporal change amount of a gait posture. The control unit further includes a gait posture determination unit that determines the gait posture based on the value of the index calculated by the third calculation unit. The fourth calculation unit further calculates the temporal change amount of the gait posture determined by the gait posture determination unit. The determination unit determines the degree of change, including a posture change degree in the temporal change of the gait posture, based on the temporal change amount calculated by the fourth calculation unit.

Further preferably, the correlation relationship is indicated by a multi regression formula that is a relational expression between the values of the characteristic factors serving as a response variable and the value of the index serving as an explaining variable, obtained through a multi regression analysis.

Further preferably, the characteristic points include a first characteristic point when a first foot touches the ground and a second characteristic point when the trajectory reaches the highest position while the user is standing on the first foot, as well as a third characteristic point when a second foot touches the ground and a fourth characteristic point when the trajectory reaches the highest position while the user is standing on the second foot.

The characteristic factors include a first characteristic factor that is a distance between the first characteristic point and the second characteristic point in the vertical direction in the trajectory projected onto the plane that is perpendicular or substantially perpendicular to the advancement direction, and a second characteristic factor that is calculated from a distance between the first characteristic point and the second characteristic point and a distance between the third characteristic point and the fourth characteristic point in the trajectory projected onto the plane that is perpendicular or substantially perpendicular to the horizontal direction.

The index includes a step size. The multi regression formula is a formula that calculates the sum of the product of a first partial regression coefficient obtained through the multi regression analysis and the first characteristic factor, the product of a second partial regression coefficient obtained through the multi regression analysis and the second characteristic factor, and a third partial regression coefficient.

Further preferably, the characteristic points include a first characteristic point when a first foot touches the ground, a second characteristic point when the trajectory reaches the highest position while the user is standing on the first foot, a third characteristic point furthest to the right in the trajectory, and a fourth characteristic point furthest to the left in the trajectory, as well as a fifth characteristic point furthest forward on the right side in the trajectory, a sixth characteristic point furthest forward on the left side in the trajectory, a seventh characteristic point furthest rearward on the right side in the trajectory, and an eighth characteristic point furthest rearward on the left side in the trajectory.

The characteristic factors include a first characteristic factor that is a quotient obtained by dividing a distance between the first characteristic point and the second characteristic point in the vertical direction in the trajectory projected onto the plane that is perpendicular or substantially perpendicular to the advancement direction, by a distance between the third characteristic point and the fourth characteristic point in the horizontal direction, and a second characteristic factor that is a quotient obtained by dividing a distance between the fifth characteristic point and the sixth characteristic point in the horizontal direction in the trajectory projected onto the plane that is perpendicular or substantially perpendicular to the vertical direction, by a distance between the seventh characteristic point and the eighth characteristic point in the horizontal direction.

The index includes the step spacing. The multi regression formula is a formula that calculates the sum of the product of a first partial regression coefficient obtained through the multi regression analysis and the first characteristic factor, the product of a second partial regression coefficient obtained through the multi regression analysis and the second characteristic factor, and a third partial regression coefficient.

According to a preferred embodiment of the present invention, with the gait change determination device, a trajectory of the user's predetermined area on which the main body unit is worn is specified during walking based on accelerations detected by the accelerometer, the temporal change amount of the trajectory is specified, and the degree of change, which is the degree of the temporal change, is calculated and determined based on the calculated temporal change.

Accordingly, the degree of the temporal change in the trajectory of the user's predetermined area is calculated, making the device less susceptible to the influence of the user simply changing his/her movement speed or the influence of differences among individual users. As a result, it is possible to provide a gait change determination device that is capable of more accurately determining a degree of change in a gait.

The above and other elements, features, steps, characteristics and advantages of the present invention will become more apparent from the following detailed description of the preferred embodiments with reference to the attached drawings.

BRIEF DESCRIPTION OF THE DRAWINGS

FIGS. 5A through 5F are diagrams illustrating multiple examples of the trajectory of a user's waist when walking, as seen from the direction in which the walking advances.

FIGS. 6A-6C are diagrams illustrating a correlation between the trajectory of the user's waist when walking as calculated from acceleration data and the trajectory of the user's waist as actually measured, according to a preferred embodiment of the present invention.

FIGS. 7A and 7B are diagrams illustrating characteristic points contained in a pattern of a trajectory projected onto an XY plane, according to a preferred embodiment of the present invention.

FIGS. 8A and 8B are diagrams illustrating characteristic points contained in a pattern of a trajectory projected onto an XZ plane, according to a preferred embodiment of the present invention.

FIGS. 10A and 10B are diagrams illustrating characteristic factors calculated based on the positions of characteristic points contained in a pattern of a trajectory projected onto an XY plane, according to a preferred embodiment of the present invention.

FIGS. 11A and 11B are diagrams illustrating characteristic factors calculated based on the positions of characteristic points contained in a pattern of a trajectory projected onto an XZ plane, according to a preferred embodiment of the present invention.

FIGS. 13A and 13B are first diagrams illustrating a correlation relationship between a characteristic factor and a step size serving as an index indicating a gait posture, according to a preferred embodiment of the present invention.

FIGS. 14A and 14B are second diagrams illustrating a correlation relationship between a characteristic factor and a step size serving as an index indicating a gait posture, according to a preferred embodiment of the present invention.

DETAILED DESCRIPTION OF THE PREFERRED EMBODIMENTS

Figure 1:
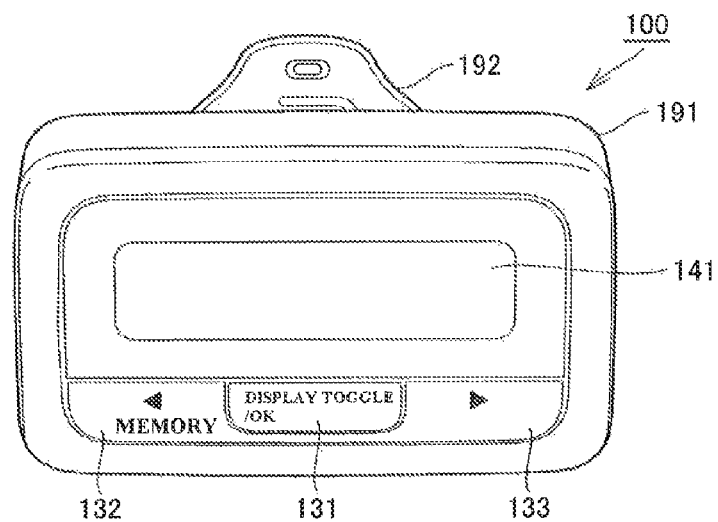
FIG. 1 is an external view of an activity meter according to a preferred embodiment of the present invention.

Hereinafter, preferred embodiments of the present invention will be described in detail with reference to the drawings. Note that identical or corresponding elements in the diagrams will be given the same reference numerals, and descriptions thereof will not be repeated.

The present preferred embodiment will be described assuming that a gait posture determination apparatus is embodied as an activity meter capable not only of measuring a number of steps, but also of measuring an activity amount (also called an "exercise amount") during exercise and during daily activities (for example, vacuuming, carrying light objects, cooking, and so on). However, the gait posture determination apparatus is not limited thereto, and may be a pedometer capable of measuring a number of steps, for example.

FIG. 1 is an external view of an activity meter 100 according to this preferred embodiment of the present invention. As shown in FIG. 1, the activity meter 100 preferably includes a main body unit 191 and a clip unit 192. The clip unit 192 is used to affix the activity meter 100 to the clothing or the like of a user.

A display toggle/OK switch 131, a left operation/memory switch 132, and a right operation switch 133 that configure part of an operation unit 130, mentioned later, and a display 141 that configures part of a display unit 140, also mentioned later, are provided in the main body unit 191.

Although the display 141 is described as being configured of a liquid-crystal display (LCD) in the present preferred embodiment, the display 141 is not limited thereto, and may be another type of display, such as an electroluminescence (EL) display, for example.

Figure 2:
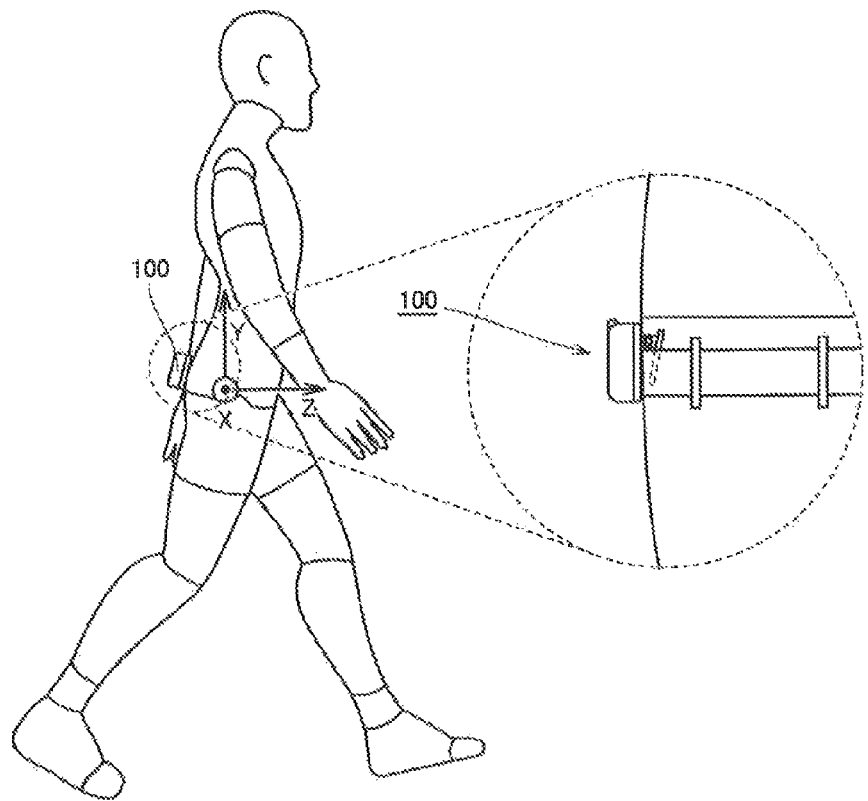
FIG. 2 is a diagram illustrating a state in which the activity meter according to a preferred embodiment of the present invention is used.

FIG. 2 is a diagram illustrating an example of a usage state of the activity meter 100 according to this preferred embodiment. As shown in FIG. 2, the activity meter 100 is affixed to, for example, a belt around the waist of the user using the clip unit 192. In this preferred embodiment, it is desirable for the activity meter 100 to be affixed to and worn in the vicinity of the user's waist.

Note that in the present preferred embodiment, a coordinate system is used in which the direction in which the user advances while walking is taken as the Z axis (where the direction the user is advancing is the forward direction), the user's left and right directions while walking are taken as the X axis (where the right direction is the forward direction), and the vertical direction is taken as the Y axis (where the upward direction is the forward direction).

Figure 3B:
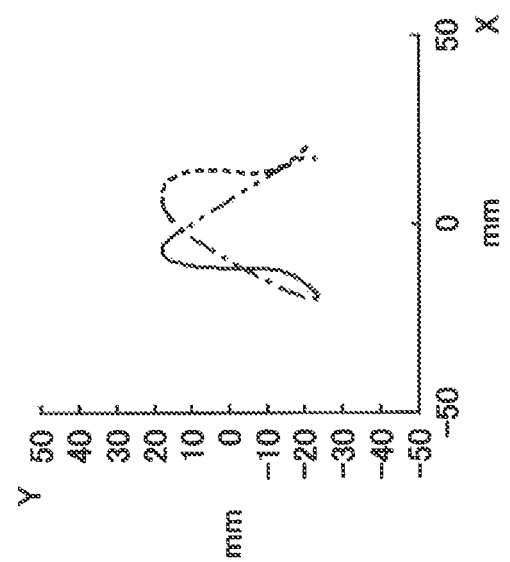
FIGS. 3A and 3B are diagrams illustrating a first example of the trajectory of a user's waist when walking, as seen from the direction in which the walking advances.
Figure 3A:
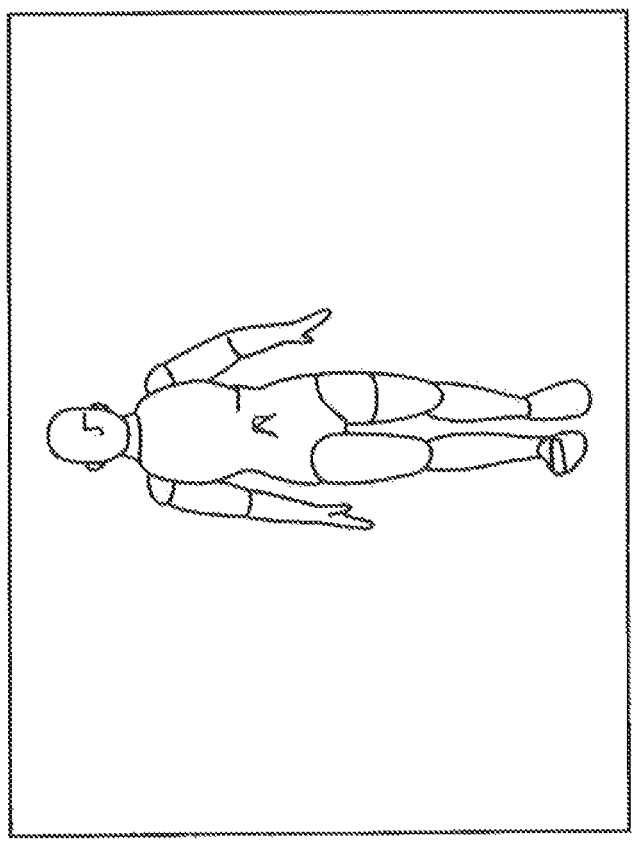
Figure 4A:
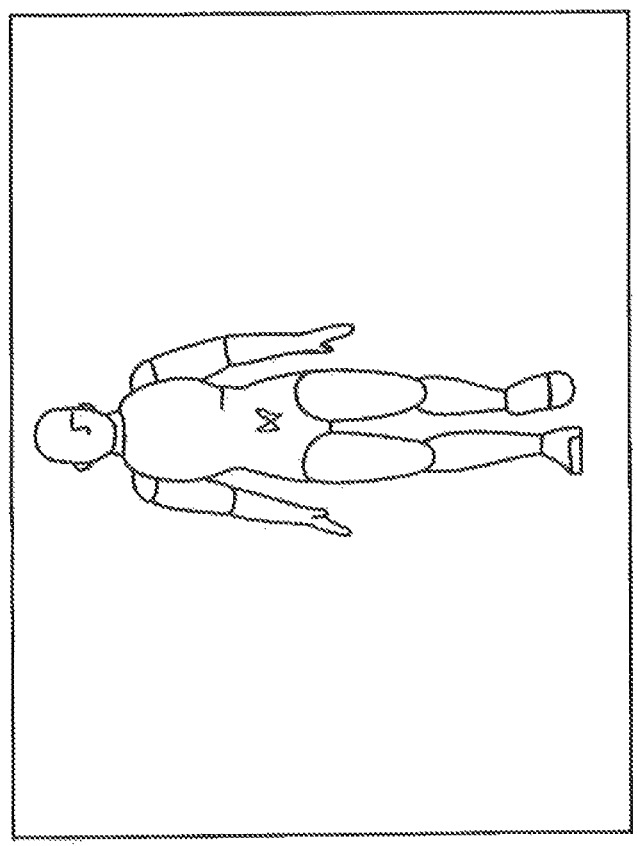
FIGS. 4A and 4B are diagrams illustrating a second example of the trajectory of a user's waist when walking, as seen from the direction in which the walking advances.
Figure 4B:
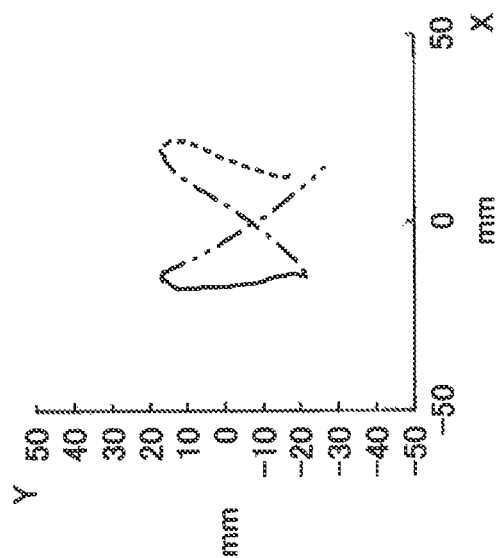

FIGS. 3A and 3B are diagrams illustrating a first example of the trajectory of the user's waist when walking, as seen from the direction in which the walking advances. FIGS. 4A and 4B are diagrams illustrating a second example of the trajectory of the user's waist when walking, as seen from the direction in which the walking advances. FIGS. 3A and 4A are diagrams in which the trajectory of the waist when walking is overlaid on an image of the user. FIGS. 3B and 4B, meanwhile, are diagrams expressing the trajectory of the user's waist when walking as graphs.

As shown in FIGS. 3A through 4B, the trajectories are trajectories during walking that have been projected onto an XY plane that is a plane perpendicular or substantially perpendicular to the Z axis. Normally, during walking, the feet are moved through a process in which the right foot leaves the ground, reaches the highest position for the right foot, and then once again makes contact with the ground, after which the left foot leaves the ground, reaches the highest position for the left foot, and then once again makes contact with the ground.

During such a walking process, the trajectory of the user's waist follows a specific pattern, in which the waist first progresses from the lower-right to the upper-left, reaches the highest position on the upper-left, progresses toward the lower-left, reaches the lowest position on the lower-left, progresses toward the upper-right, reaches the highest position on the upper-right, progresses toward the lower-right, and reaches the lowest position on the lower-right.

FIGS. 5A through 5F are diagrams illustrating multiple examples of the trajectory of the user's waist when walking, as seen from the direction in which the walking advances. FIG. 5A is the same diagram as that shown in FIG. 3B. FIG. 5A illustrates the trajectory of the user's waist when walking, when the user is in a normal gait posture. FIG. 5B is the same diagram as that shown in FIG. 4B. FIG. 5B illustrates the trajectory of the user's waist when walking, when the step spacing is wider, or more "bowlegged", then the case shown in FIG. 5A.

FIG. 5C illustrates the trajectory of the user's waist when walking, when the step spacing is narrower then the case shown in FIG. 5A. FIG. 5D illustrates the trajectory of the user's waist when walking, when the user is shuffling his/her feet more than in the case shown in FIG. 5A. FIG. 5E illustrates the trajectory of the user's waist when walking, when the user is walking in a more slouched position than in the case shown in FIG. 5A. FIG. 5F illustrates the trajectory of the user's waist when walking, when the user is walking with longer strides than in the case shown in FIG. 5A.

In this manner, although the trajectories shown in FIGS. 5A through 5F appear to be different, they all have a specific pattern, as illustrated in FIGS. 3A through 4B.

FIGS. 6A-6C are diagrams illustrating a correlation between the trajectory of the user's waist when walking as calculated from acceleration data in the trajectory of the user's waist as actually measured, according to this preferred embodiment. FIG. 6A is a diagram illustrating the trajectory of the user's waist when walking, as seen from the direction in which the walking advances, as actually measured. FIG. 6A corresponds to the diagrams in FIGS. 3B, 4B, and 5A through 5F.

The trajectory shown in FIG. 6A is obtained by, for example, using a camera to capture an image of the user walking from the direction in which the user is advancing and connecting the movement of a point in the vicinity of the waist through image processing.

FIG. 6B is a diagram illustrating the trajectory of the user's waist when walking, as seen from the direction in which the walking advances, as calculated from acceleration data. Here, a method for calculating the trajectory of the user's waist based on acceleration data from three axial directions that are detected by an accelerometer in the activity meter 100 will be described. Note that this trajectory is calculated by a control unit of the activity meter 100.

First, accelerations $Ax(t)$, $Ay(t)$, and $Az(t)$ are specified for the X axis, Y axis, and Z axis directions, respectively, shown in FIG. 2. Here, in the case where the three axial directions of the accelerometer match the directions of the X axis, Y axis, and Z axis, detection values obtained by the accelerometer may be taken as-is as the accelerations $Ax(t)$, $Ay(t)$, and $Az(t)$ for the X axis, Y axis, and Z axis directions, respectively. On the other hand, in the case where the three axial directions of the accelerometer do not match the directions of the X axis, Y axis, and Z axis, the detection values obtained by the accelerometer are converted into coordinates in order to calculate the accelerations Ax(t), Ay(t), and Az(t) for the X axis, Y axis, and Z axis directions, respectively.

Next, by integrating the accelerations Ax(t), Ay(t), and Az(t) using Formulas (1) through (3), velocities Vx(t), Vy(t), and Vz(t) are calculated for the X axis, Y axis, and Z axis directions, respectively.

$$Vx(t) = \int Ax(t)dt \quad \text{Equation 1}$$

$$Vy(t) = \int Ay(t)dt \quad \text{Equation 2}$$

$$Vz(t) = \int Az(t)dt \quad \text{Equation 3}$$

Next, velocities in which average velocity components in a short amount of time between ±1 steps, or in other words, relative velocities Vx'(t), Vy'(t), and Vz'(t) relative to the average velocities in the short amount of time, are calculated using Formulas (4) through (6). Note that here, the time of a single step is taken as T seconds, and T is calculated by, for example, calculating the time between acceleration peaks on a step-by-step basis.

$$V'x(t) = Vx(t) - \overline{Vx(t)} = Vx(t) - \tfrac{1}{2}\int_{t-T}^{t+T} Ay(t)dt \quad \text{Equation 4}$$

$$V'y(t) = Vy(t) - \overline{Vy(t)} = Vy(t) - \tfrac{1}{2}\int_{t-T}^{t+T} Ax(t)dt \quad \text{Equation 5}$$

$$V'z(t) = Vz(t) - \overline{Vz(t)} = Vz(t) - \tfrac{1}{2}\int_{t-T}^{t+T} Az(t)dt \quad \text{Equation 6}$$

Finally, relative positions X(t), Y(t), and Z(t) relative to average positions in the short amount of time are calculated for the X axis, Y axis, and Z axis directions, respectively, by integrating the relative velocities Vx'(t), Vy'(t), and Vz'(t) using Formulas (7) through (9), respectively.

$$X(t) = \int V'x(t)dt \quad \text{Equation 7}$$

$$Y(t) = \int V'y(t)dt \quad \text{Equation 8}$$

$$Z(t) = \int V'z(t)dt \quad \text{Equation 9}$$

A trajectory in which the user's trajectory when walking is projected onto an XY plane is obtained by plotting points (X(t), Y(t)), corresponding to the positions X(t) and Y(t) calculated as described above being assigned to X, Y coordinate values, on an XY plane while varying t. An example of this trajectory is the trajectory shown in FIG. 6B.

Likewise, a trajectory in which the user's trajectory when walking is projected onto an XZ plane is obtained by plotting points (X(t), Z(t)), corresponding to the positions X(t) and Z(t) being assigned to X, Z coordinate values, on an XZ plane while varying t.

Furthermore, a trajectory in which the user's trajectory when walking is projected onto a YZ plane is obtained by plotting points (Y(t), Z(t)), corresponding to the positions Y(t) and Z(t) being assigned to Y, Z coordinate values, on a YZ plane while varying t.

These trajectories are trajectories having patterns such as those shown in FIGS. 7A through 9A, respectively, which will be discussed later.

FIG. 6C is a graph illustrating a correlation relationship between the height (width in the Y axis direction) of the actually-measured trajectory and the height (width in the Y axis direction) of the trajectory calculated from the detected acceleration data. In this manner, the respective heights are plotted for cases where the user walks with various types of gaits. Then, a regression analysis is performed, with the height of the actually-measured trajectory taken as y, the height of the calculated trajectory taken as x, and the regression formula taken as y=0.9878x+0.3452, resulting in a coefficient of determination R2 of 0.9575, for example.

Based on this, the trajectories calculated from the acceleration data can be said to match the actually-measured trajectories at a very high level of accuracy.

Figure 9:
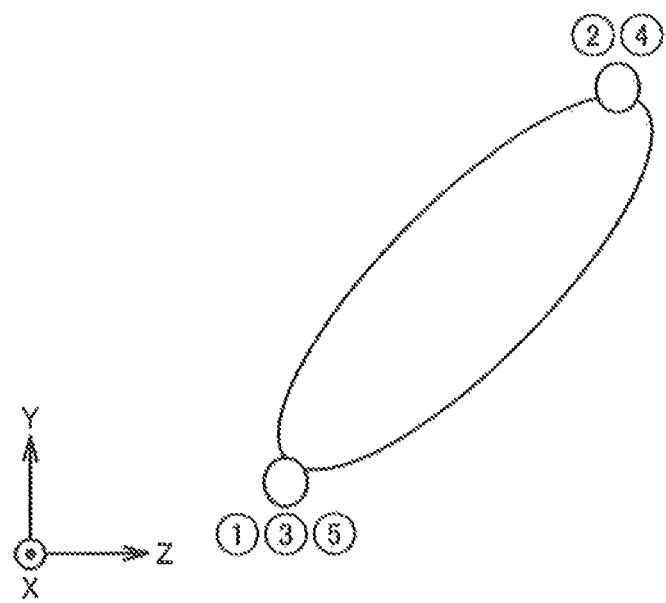
FIG. 9 is a diagram illustrating characteristic points contained in a pattern of a trajectory projected onto a YZ plane, according to a preferred embodiment of the present invention.

FIGS. 7A and 7B are diagrams illustrating characteristic points contained in the pattern of the trajectory projected onto the XY plane, according to the present preferred embodiment. FIGS. 8A and 8B are diagrams illustrating characteristic points contained in the pattern of the trajectory projected onto the XZ plane, according to the present preferred embodiment. FIG. 9 is a diagram illustrating characteristic points contained in the pattern of the trajectory projected onto the YZ plane, according to the present preferred embodiment.

As shown in FIGS. 7A and 7B, a characteristic point (1) is a point in the gait cycle where the right foot touches the ground. Conditions for specifying the characteristic point (1) are that the point is on the right in the horizontal and is lowest on the vertical.

A characteristic point (2) is a point in the gait cycle where the user is standing on his/her right foot (and particularly, where the user's waist is at the highest position in the vertical direction). Conditions for specifying the characteristic point (2) are that the point follows the characteristic point (1) and is highest on the vertical.

A characteristic point (3) is a point in the gait cycle where the left foot touches the ground. Conditions for specifying the characteristic point (3) are that the point follows the characteristic point (2) and is lowest on the vertical.

A characteristic point (4) is a point in the gait cycle where the user is standing on his/her left foot (and particularly, where the user's waist is at the highest position in the vertical direction). Conditions for specifying the characteristic point (4) are that the point follows the characteristic point (3) and is highest on the vertical.

A characteristic point (5) is a point in the gait cycle where the right foot touches the ground. Conditions for specifying the characteristic point (5) are that the point follows the characteristic point (4) and is lowest on the vertical. Note that the characteristic point (5) is also the characteristic point (1) for the next cycle.

A characteristic point (6) is a point in the gait cycle where the user's waist is furthest to the right. A condition for specifying the characteristic point (6) is that the value of X(t) calculated through Formula (7) is the highest where X(t)≥0 in a single cycle.

A characteristic point (7) is a point in the gait cycle where the user's waist is furthest to the left. A condition for specifying the characteristic point (7) is that the value of X(t) calculated through Formula (7) is the lowest where X(t)<0 in a single cycle.

A characteristic point (8) is an intersecting point, in the gait cycle, that is in the trajectory of the waist in a single cycle of walking. A condition for specifying the characteristic point (8) is that the point is a point in the XY plane at which the trajectory of the waist from the characteristic point (2) to the characteristic point (3) and the trajectory of the waist from the characteristic point (4) to the characteristic point (5) intersect.

As shown in FIGS. 8A and 8B, a characteristic point (9) is a point where the right foot touches the ground in the gait cycle. Conditions for specifying the characteristic point (9) are that the point is on the right in the horizontal and is rearmost in the depth direction.

A characteristic point (10) is a point in the gait cycle where the user is standing on his/her right foot (and particularly, a point when the user's waist is at the forwardmost position relative to the average position in the direction in which the user is advancing in the short amount of time). Conditions for specifying the characteristic point (10) are that the point follows the characteristic point (9) and is forwardmost in the depth direction.

A characteristic point (11) is a point in the gait cycle where the left foot touches the ground. Conditions for specifying the characteristic point (11) are that the point follows the characteristic point (10) and is rearmost in the depth direction.

A characteristic point (12) is a point in the gait cycle where the user is standing on his/her left foot (and particularly, a point when the user's waist is at the forwardmost position relative to the average position in the direction in which the user is advancing in the short amount of time). Conditions for specifying the characteristic point (12) are that the point follows the characteristic point (11) and is forwardmost in the depth direction.

A characteristic point (13) is a point in the gait cycle where the right foot touches the ground. Conditions for specifying the characteristic point (11) are that the point follows the characteristic point (12) and is rearmost in the depth direction. Note that the characteristic point (13) is also the characteristic point (9) for the next cycle.

A characteristic point (14) is an intersecting point, in the gait cycle, that is in the trajectory of the waist in a single cycle of walking. A condition for specifying the characteristic point (14) is that the point is a point in the XZ plane at which the trajectory of the waist from the characteristic point (10) to the characteristic point (11) and the trajectory of the waist from the characteristic point (12) to the characteristic point (13) intersect.

In FIG. 9, the characteristic points (1), (3), and (5) described with reference to FIGS. 7A and 7B are the lowermost points in the pattern of the trajectory projected onto the YZ plane. Likewise, the characteristic points (2) and (4) are the uppermost points in the pattern of the trajectory projected onto the YZ plane.

Figures 12A, 12B:
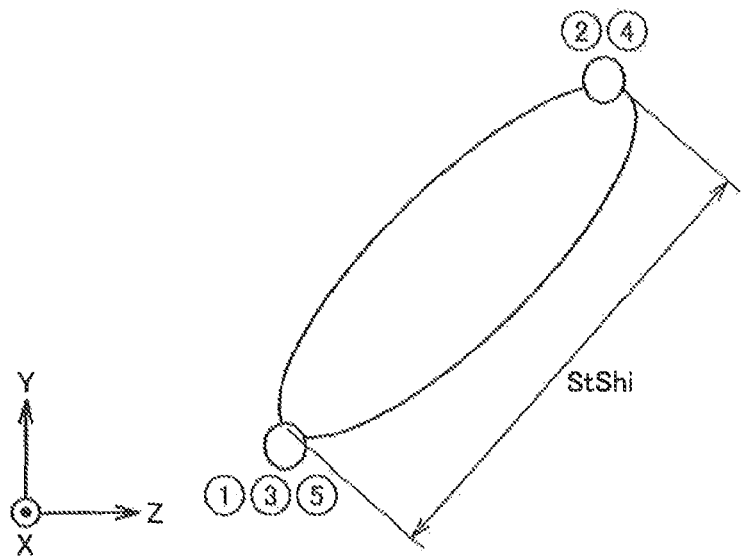
FIGS. 12A and 12B are diagrams illustrating characteristic factors calculated based on the positions of characteristic points contained in a pattern of a trajectory projected onto a YZ plane, according to a preferred embodiment of the present invention.

FIGS. 10A and 10B are diagrams illustrating characteristic factors calculated based on the positions of the characteristic points contained in the pattern of the trajectory projected onto the XY plane, according to the present preferred embodiment. FIGS. 11A and 11B are diagrams illustrating characteristic factors calculated based on the positions of the characteristic points contained in the pattern of the trajectory projected onto the XZ plane, according to the present preferred embodiment. FIGS. 12A and 12B are diagrams illustrating characteristic factors calculated based on the positions of the characteristic points contained in the pattern of the trajectory projected onto the YZ plane, according to the preferred embodiment.

As shown in FIGS. 10A and 10B, a characteristic factor Wu is a distance between the characteristic point (2) and the characteristic point (4) in the X axis direction of the XY plane (called an "upper-side horizontal width"), and is calculated by subtracting the X coordinate value of the characteristic point (4) from the X coordinate value of the characteristic point (2).

A characteristic factor Wd is a distance between the characteristic point (1) and the characteristic point (3) in the X axis direction of the XY plane (called a "lower-side horizontal width"), and is calculated by subtracting the X coordinate value of the characteristic point (3) from the X coordinate value of the characteristic point (1).

A characteristic factor W is a distance between the characteristic point (6) and the characteristic point (7) in the X axis direction of the XY plane (called a "horizontal width"), and is calculated by subtracting the X coordinate value of the characteristic point (7) from the X coordinate value of the characteristic point (6).

A characteristic factor Hl is a distance between the characteristic point (4) and the characteristic point (3) in the Y axis direction of the XY plane (called a "left-side vertical width"), and is calculated by subtracting the Y coordinate value of the characteristic point (3) from the Y coordinate value of the characteristic point (4).

A characteristic factor Hr is a distance between the characteristic point (2) and the characteristic point (1) in the Y axis direction of the XY plane (called a "right-side vertical width"), and is calculated by subtracting the Y coordinate value of the characteristic point (1) from the Y coordinate value of the characteristic point (2).

A characteristic factor H is the average of the characteristic factor Hl and the characteristic factor Hr in the XY plane (called a "vertical width"), and is calculated by adding Hl and Hr and dividing the result by 2.

A characteristic factor Hcl is the height of the characteristic point (8) relative to the characteristic point (3) in the XY plane (called a "left-side cross point height"), and is calculated by subtracting the Y coordinate value of the characteristic point (3) from the Y coordinate value of the characteristic point (8).

A characteristic factor Hcr is the height of the characteristic point (8) relative to the characteristic point (1) in the XY plane (called a "right-side cross point height"), and is calculated by subtracting the Y coordinate value of the characteristic point (1) from the Y coordinate value of the characteristic point (8).

A characteristic factor ISO is the height of the characteristic point (8) relative to the vertical width of the trajectory in the XY plane (called a "phase"), and is calculated by dividing the characteristic factor Hcl by the characteristic factor Hl, dividing the characteristic factor Hcr by the characteristic factor Hr, adding the results of the divisions together, and dividing that result by 2.

A characteristic factor Vlev indicates the degree to which the trajectory in the XY plane is open on the upper side or on the lower side (called a "shape V or Λ"), and is calculated by dividing the characteristic factor Wu by the characteristic factor Wd.

A characteristic factor Ilev is a factor for specifying whether the shape of the trajectory in the XY plane is longer vertically or longer horizontally (called a "shape I" hereinafter), and is calculated by dividing the characteristic factor H by the characteristic factor W.

A characteristic factor Hb is a ratio between the horizontal and the vertical in the XY plane (called a "right/left vertical width ratio"), and is calculated by dividing the characteristic factor Hr by the characteristic factor Hl.

A characteristic factor Yb is a ratio between the left/right heights in the XY plane (called a "left/right height ratio"), and is calculated by dividing a difference between the Y coordinate value of the characteristic point (4) and the Y coordinate value of the characteristic point (1) by a difference between the Y coordinate value of the characteristic point (2) and the Y coordinate value of the characteristic point (3).

A characteristic factor Wb is a ratio between the left/right widths in the XY plane (called a "left/right width ratio"), and is calculated by dividing a difference between the X coordinate value of the characteristic point (6) and the X coordinate value of the characteristic point (8) by a difference between the X coordinate value of the characteristic point (8) and the X coordinate value of the characteristic point (7).

A characteristic factor Stl is the total vertical amplitude in the XY plane from when the right foot touches the ground to when the left foot touches the ground (called a "vertical amplitude from right foot contact to left foot contact"), and is calculated by subtracting the Y coordinate value of the characteristic point (1) from the Y coordinate value of the characteristic point (2), subtracting the Y coordinate value of the characteristic point (3) from the Y coordinate value of the characteristic point (2), and adding the results of the subtractions together.

A characteristic factor Str is the total vertical amplitude in the XY plane from when the left foot touches the ground to when the right foot touches the ground (called a "vertical amplitude from left foot contact to right foot contact"), and is calculated by subtracting the Y coordinate value of the characteristic point (3) from the Y coordinate value of the characteristic point (4), subtracting the Y coordinate value of the characteristic point (5) from the Y coordinate value of the characteristic point (4), and adding the results of the subtractions together.

A characteristic factor jun is a factor indicating whether the trajectory traces the clockwise direction or traces the counterclockwise direction (called a "trace order"), and is calculated through a positive-negative determination on the X coordinates of the characteristic point (2) and the characteristic point (4).

As shown in FIGS. 11A and 11B, a characteristic factor WuSu is a distance between the characteristic point (10) and the characteristic point (12) in the X axis direction of the XZ plane (called an "upper-side horizontal width"), and is calculated by subtracting the X coordinate value of the characteristic point (10) from the X coordinate value of the characteristic point (12).

A characteristic factor WdSu is a distance between the characteristic point (9) and the characteristic point (11) in the X axis direction of the XZ plane (called a "lower-side horizontal width"), and is calculated by subtracting the X coordinate value of the characteristic point (11) from the X coordinate value of the characteristic point (9).

A characteristic factor Wsu is a distance between the characteristic point (6) and the characteristic point (7) in the X axis direction of the XZ plane (called a "horizontal width"), and is calculated by subtracting the X coordinate value of the characteristic point (7) from the X coordinate value of the characteristic point (6).

A characteristic factor HlSu is a distance between the characteristic point (12) and the characteristic point (11) in the Z axis direction of the XZ plane (called a "left-side vertical width"), and is calculated by subtracting the Z coordinate value of the characteristic point (11) from the Z coordinate value of the characteristic point (12).

A characteristic factor HrSu is a distance between the characteristic point (10) and the characteristic point (9) in the Z axis direction of the XZ plane (called a "right-side vertical width"), and is calculated by subtracting the Z coordinate value of the characteristic point (9) from the Z coordinate value of the characteristic point (10).

A characteristic factor Hsu is the average of the characteristic factor HlSu and the characteristic factor HrSu in the XZ plane (called a "vertical width"), and is calculated by adding HlSu and HrSu and dividing the result by 2.

A characteristic factor HclSu is the height of the characteristic point (8) relative to the characteristic point (11) in the XZ plane (called a "left-side cross point height"), and is calculated by subtracting the Z coordinate value of the characteristic point (11) from the Z coordinate value of the characteristic point (8).

A characteristic factor HcrSu is the height of the characteristic point (8) relative to the characteristic point (9) in the XZ plane (called a "right-side cross point height"), and is calculated by subtracting the Z coordinate value of the characteristic point (9) from the Z coordinate value of the characteristic point (8).

A characteristic factor ISOSu is the height of the characteristic point (14) relative to the vertical width of the trajectory in the XZ plane (called a "phase"), and is the same value as the ISO in the XY plane described with reference to FIGS. 10A and 10B.

A characteristic factor VlevSu indicates the degree to which the trajectory in the XZ plane is open on the upper side or on the lower side (called a "shape V or Λ"), and is calculated by dividing the characteristic factor WuSu by the characteristic factor WdSu.

A characteristic factor IlevSu is a factor for specifying whether the shape of the trajectory in the XZ plane is longer vertically or longer horizontally (called a "shape I" hereinafter), and is calculated by dividing the characteristic factor Hsu by the characteristic factor Wsu.

A characteristic factor HbSu is a ratio between the horizontal and the vertical in the XZ plane (called a "right/left vertical width ratio"), and is calculated by dividing the characteristic factor HrSu by the characteristic factor HlSu.

A characteristic factor YbSu is a ratio between the left/right heights in the XZ plane (called a "left/right height ratio"), and is calculated by dividing a difference between the Z coordinate value of the characteristic point (13) and the Z coordinate value of the characteristic point (9) by a difference between the Z coordinate value of the characteristic point (10) and the Z coordinate value of the characteristic point (11).

A characteristic factor WbSu is a ratio between the left/right widths in the XZ plane (called a "left/right width ratio"), and is the same value as Wb in the XY plane, described with reference to FIGS. 10A and 10B.

A characteristic factor StlSu is the total depth direction amplitude in the XZ plane from when the right foot touches the ground to when the left foot touches the ground (called a "depth direction amplitude from right foot contact to left foot contact"), and is calculated by subtracting the Z coordinate value of the characteristic point (9) from the Z coordinate value of the characteristic point (10), subtracting the Z coordinate value of the characteristic point (11) from the Z coordinate value of the characteristic point (10), and adding the results of the subtractions together.

A characteristic factor StrSu is the total depth direction amplitude in the XZ plane from when the left foot touches the ground to when the right foot touches the ground (called a "depth direction amplitude from left foot contact to right foot contact"), and is calculated by subtracting the Z coordinate value of the characteristic point (11) from the Z coordinate value of the characteristic point (12), subtracting the Z coordinate value of the characteristic point (13) from the Z coordinate value of the characteristic point (12), and adding the results of the subtractions together.

A characteristic factor Zfl is the space in the XZ plane that the waist moves in the depth direction after reaching its highest point when the user is standing on his/her left foot (called a "waist depth direction movement from highest point when standing on left foot"), and is calculated by subtracting the Z coordinate value of the characteristic point (4) from the Z coordinate value of the characteristic point (12).

A characteristic factor Zfr is the space in the XZ plane that the waist moves in the depth direction after reaching its highest point when the user is standing on his/her right foot (called a "waist depth direction movement from highest point when standing on right foot"), and is calculated by subtracting the Z coordinate value of the characteristic point (2) from the Z coordinate value of the characteristic point (10).

A characteristic factor Zf is the space in the XZ plane that the waist moves in the depth direction after reaching its highest point when the user is standing erect (called a "waist depth direction movement from highest point when standing erect"), and is calculated by adding the characteristic factor Zfl and the characteristic factor Zfr and dividing the result by 2.

A characteristic factor Zbl is the space in the XZ plane that the waist moves in the depth direction after the left foot touches the ground (called a "waist depth direction movement from left foot contact"), and is calculated by subtracting the Z coordinate value of the characteristic point (3) from the Z coordinate value of the characteristic point (11).

A characteristic factor Zbr is the space in the XZ plane that the waist moves in the depth direction after the right foot touches the ground (called a "waist depth direction movement from right foot contact"), and is calculated by subtracting the Z coordinate value of the characteristic point (5) from the Z coordinate value of the characteristic point (9).

A characteristic factor Zb is the space in the XZ plane that the position of the waist moves in the depth direction after a foot touches the ground (called a "waist depth direction movement from ground contact"), and is calculated by adding the characteristic factor Zbl and the characteristic factor Zbr and dividing the result by 2.

As shown in FIGS. 12A and 12B, a characteristic factor dZ is a tilt in the depth direction in the YZ plane (called a "depth direction tilt"), and is calculated by subtracting the Y coordinate value of the characteristic point (1) from the Y coordinate value of the characteristic point (2), subtracting the Z coordinate value of the characteristic point (1) from the Z coordinate value of the characteristic point (2), and dividing the result of the former by the result of the latter.

A characteristic factor StlShi is the total left diagonal amplitude in the YZ plane (called a "left depth direction amplitude"), and is calculated by adding the distance of the characteristic point (2) and the characteristic point (1) in the YZ plane to the distance of the characteristic point (2) and the characteristic point (3) in the YZ plane. The distance of the characteristic point (2) and the characteristic point (1) in the YZ plane is calculated by taking the square of the result of subtracting the Z coordinate value of the characteristic point (1) from the Z coordinate value of the characteristic point (2), adding that square to the square of the result of subtracting the Y coordinate value of the characteristic point (1) from the Y coordinate value of the characteristic point (2), and finding the square root of the result of the addition. The distance of the characteristic point (2) and the characteristic point (3) in the YZ plane is calculated by taking the square of the result of subtracting the Z coordinate value of the characteristic point (3) from the Z coordinate value of the characteristic point (2), adding that square to the square of the result of subtracting the Y coordinate value of the characteristic point (3) from the Y coordinate value of the characteristic point (2), and finding the square root of the result of the addition.

A characteristic factor StrShi is the total right diagonal amplitude in the YZ plane (called a "right depth direction amplitude"), and is calculated by adding the distance of the characteristic point (4) and the characteristic point (3) in the YZ plane to the distance of the characteristic point (4) and the characteristic point (1) in the YZ plane. The distance of the characteristic point (4) and the characteristic point (3) in the YZ plane is calculated by taking the square of the result of subtracting the Z coordinate value of the characteristic point (3) from the Z coordinate value of the characteristic point (4), adding that square to the square of the result of subtracting the Y coordinate value of the characteristic point (3) from the Y coordinate value of the characteristic point (4), and finding the square root of the result of the addition. The distance of the characteristic point (4) and the characteristic point (1) in the YZ plane is calculated by taking the square of the result of subtracting the Z coordinate value of the characteristic point (1) from the Z coordinate value of the characteristic point (4), adding that square to the square of the result of subtracting the Y coordinate value of the characteristic point (1) from the Y coordinate value of the characteristic point (4), and finding the square root of the result of the addition.

A characteristic factor StShi is the total diagonal amplitude in the YZ plane (called a "depth direction amplitude"), and is calculated by adding the characteristic factor StlShi to the characteristic factor StrShi and dividing the result by 2.

FIGS. 13A and 13B are first diagrams illustrating a correlation relationship between a characteristic factor and a step size serving as an index indicating a gait posture, according to this preferred embodiment. FIGS. 14A and 14B are second diagrams illustrating a correlation relationship between a characteristic factor and a step size serving as an index indicating a gait posture, according to this preferred embodiment.

As shown in FIGS. 13A and 13B, data is plotted with the vertical axis (y) representing the characteristic factor Hr in the pattern of the trajectory projected onto the XZ plane as illustrated in FIGS. 10A and 10B, and the horizontal axis (x) representing values actually measured for the step size, which serves as an index indicating a gait posture. Then, a regression analysis is performed, with the regression formula taken as $y=0.0735x-41.271$, resulting in a coefficient of determination $R2$ of 0.7938.

Meanwhile, as shown in FIGS. 14A and 14B, data is plotted with the vertical axis (y) representing the characteristic factor StShi in the pattern of the trajectory projected onto the YZ plane as illustrated in FIGS. 12A and 12B, and the horizontal axis (x) representing values actually measured for the step size, which serves as the index indicating a gait posture. Then, a regression analysis is performed, with the regression formula taken as $y=0.1485x-78.963$, resulting in a coefficient of determination $R2$ of 0.8192.

In this manner, the step size, which is an index indicating the gait posture, has a high correlation with the characteristic factor Hr and the characteristic factor StShi, and thus the value of the step size can be calculated by performing a multi regression analysis through the multi regression formula "step size Length=$\alpha \times Hr + \beta \times StShi + \gamma$", in which the characteristic factor Hr and characteristic factor StShi are taken as response variables and the value of the step size is taken as an explaining variable. Note that $\alpha$, $\beta$, and $\gamma$ are partial regression coefficients obtained through the multi regression analysis.

Figure 15B:
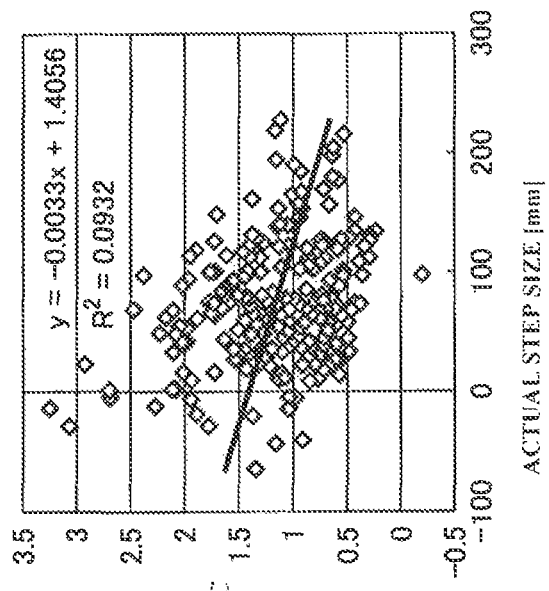
FIGS. 15A and 15B are first diagrams illustrating a correlation relationship between a characteristic factor and a step spacing serving as an index indicating a gait posture, according to a preferred embodiment of the present invention.
Figure 15A:
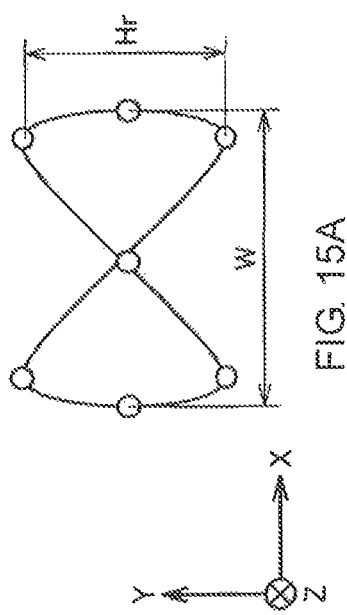
Figure 16B:
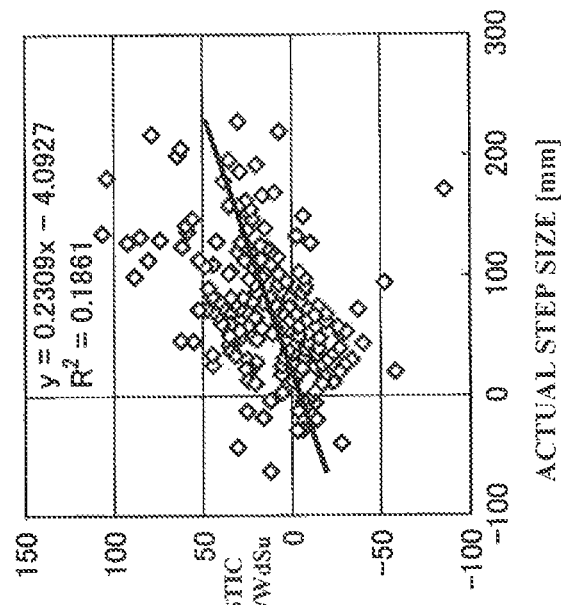
FIGS. 16A and 16B are second diagrams illustrating a correlation relationship between a characteristic factor and a step spacing serving as an index indicating a gait posture, according to a preferred embodiment of the present invention.
Figure 16A:
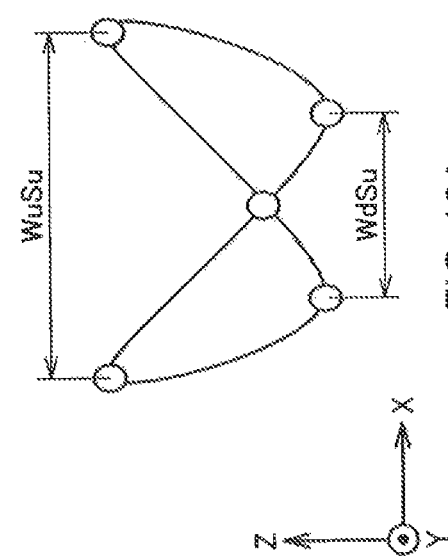

FIGS. 15A and 15B are first diagrams illustrating a correlation relationship between a characteristic factor and a step spacing serving as an index indicating a gait posture, according to this preferred embodiment. FIGS. 16A and 16B are second diagrams illustrating a correlation relationship between a characteristic factor and a step spacing serving as an index indicating a gait posture, according to this preferred embodiment.

As shown in FIGS. 15A and 15B, data is plotted with the vertical axis (y) representing a characteristic factor Hr/W in which the characteristic factor Hr in the pattern of the trajectory projected onto the XZ plane as illustrated in FIGS. 10A and 10B is divided by the characteristic factor W, and the horizontal axis (x) representing values actually measured for the step spacing, which serves as an index indicating a gait posture. Then, a regression analysis is performed, with the regression formula taken as $y=0.0033x-1.4056$, resulting in a coefficient of determination $R2$ of 0.0932.

As shown in FIGS. 16A and 16B, data is plotted with the vertical axis (y) representing a characteristic factor WuSu/WdSu in which the characteristic factor WuSu in the pattern of the trajectory projected onto the XZ plane as illustrated in FIGS. 11A and 11B is divided by the characteristic factor WdSu, and the horizontal axis (x) representing values actually measured for the step spacing, which serves as an index indicating a gait posture. Then, a regression analysis is performed, with the regression formula taken as y=0.2309x−4.0927, resulting in a coefficient of determination R2 of 0.1861, for example.

The value of the step spacing, which is an index indicating the gait posture, can be calculated by performing a multi regression analysis through the multi regression formula "step spacing Width=δ×Hr/W+ε×WuSu/WdSu+ζ", in which the characteristic factor Hr/W and the characteristic factor WuSu/WdSu are taken as response variables and the value of the step size is taken as an explaining variable. Note that δ, ε, and ζ are coefficients obtained through the multi regression analysis.

Figure 17:
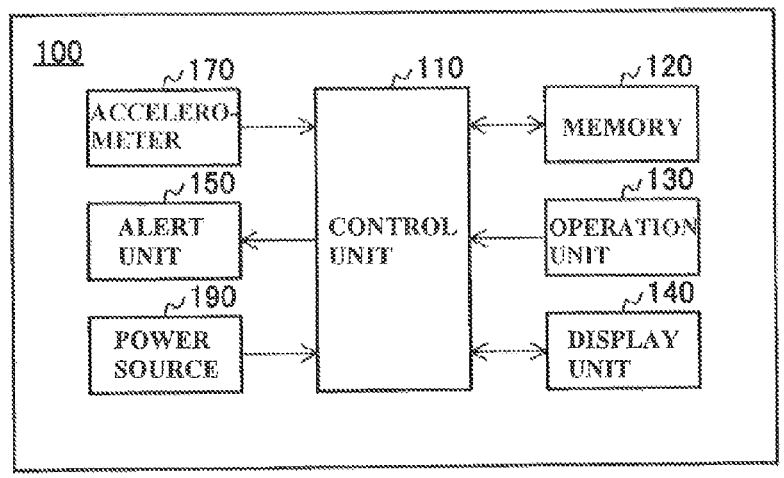
FIG. 17 is a block diagram illustrating the overall configuration of an activity meter according to a preferred embodiment of the present invention.

FIG. 17 is a block diagram illustrating the overall configuration of the activity meter 100 according to this preferred embodiment. As shown in FIG. 17, the activity meter 100 preferably includes a control unit 110, a memory 120, the operation unit 130, the display unit 140, an audio alert unit 150, an accelerometer 170, and a power source 190. The activity meter 100 may also include an interface that communicates with an external computer.

The control unit 110, the memory 120, the operation unit 130, the display unit 140, the audio alert unit 150, the accelerometer 170, and the power source 190 are preferably contained within the main body unit 191 illustrated in FIG. 1.

The operation unit 130 includes the display toggle/OK switch 131, the left operation/memory switch 132, and the right operation switch 133 illustrated in FIG. 1, and sends operation signals indicating that those switches have been manipulated to the control unit 110.

Although a semiconductor-based element that uses a MEMS (micro-electromechanical system) technique is preferably used as the accelerometer 170, the accelerometer 170 is not limited thereto, and may use a different system, such as a mechanical system or an optical system, for example. In the present preferred embodiment, the accelerometer 170 outputs, to the control unit 110, detection signals indicating accelerations in each of three axial directions. However, the accelerometer 170 is not limited to three axes, and may use one axis or two axes, for example.

The memory 120 preferably includes a non-volatile memory such as a ROM (read-only memory) (for example, a flash memory), a volatile memory such as a RAM (random access memory) (for example, an SDRAM (synchronous dynamic random access memory)), and so on.

The memory 120 stores data of programs that control the activity meter 100, data used to control the activity meter 100, configuration data used to configure various functions of the activity meter 100, data of measurement results, such as a number of steps, an activity amount, and so on, for a predetermined amount of time (for example, on a daily basis), and so on. The memory 120 is also preferably used as a working memory when programs are executed.

The control unit 110 preferably includes a CPU (central processing unit) and controls, in accordance with a program to control the activity meter 100 stored in the memory 120, the memory 120, the display unit 140, and the audio alert unit 150, based on the detection signals from the accelerometer 170 and an atmospheric pressure sensor 180, in response to an operation signal from the operation unit 130.

The display unit 140 includes the display 141 illustrated in FIG. 1, and control is carried out so that predetermined information is displayed in the display 141 in accordance with a control signal from the control unit 110.

The audio alert unit 150 carries out control, in accordance with a control signal from the control unit 110, so as to output predetermined audio from a speaker.

The power source 190 preferably includes a replaceable battery, and supplies electrical power from the battery to various units of the activity meter 100 that require electrical power to operate, such as the control unit 110.

Figure 18:
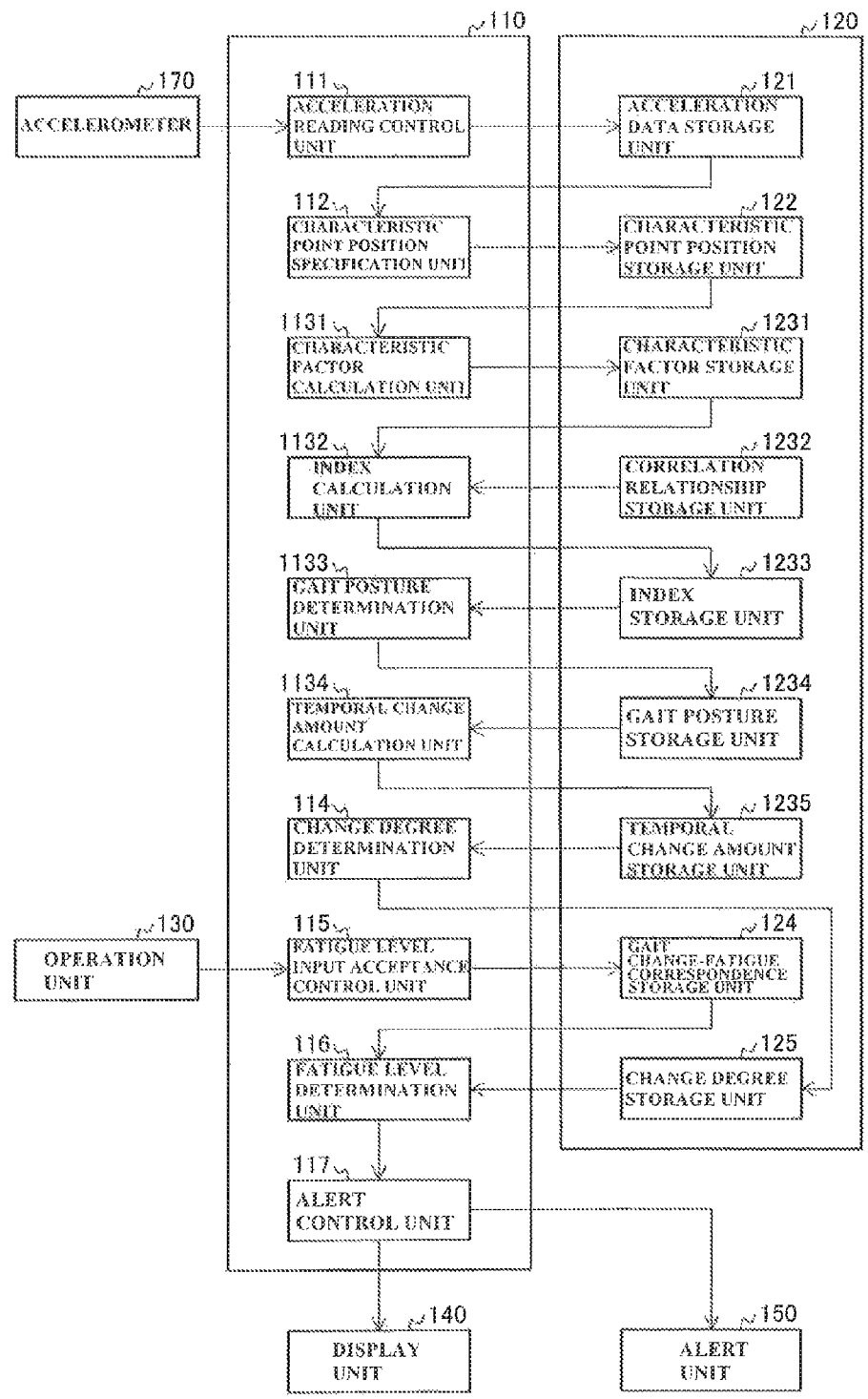
FIG. 18 is a function block diagram illustrating the overall functions of the activity meter according to a preferred embodiment of the present invention.

FIG. 18 is a function block diagram illustrating the overall functions of the activity meter 100 according to this preferred embodiment. As shown in FIG. 18, the control unit 110 of the activity meter 100 preferably includes an acceleration reading control unit 111, a characteristic point position specification unit 112, a characteristic factor calculation unit 1131, an index calculation unit 1132, a gait posture determination unit 1133, a temporal change amount calculation unit 1134, a change degree determination unit 114, a fatigue level input acceptance control unit 115, a fatigue level determination unit 116, and an alert control unit 117.

In addition, the memory 120 of the activity meter 100 includes an acceleration data storage unit 121, a characteristic point position storage unit 122, a characteristic factor storage unit 1231, a correlation relationship storage unit 1232, an index storage unit 1233, a gait posture storage unit 1234, a temporal change amount storage unit 1235, a gait change-fatigue correspondence storage unit 124, and a change degree storage unit 125.

Note that in the present preferred embodiment, it is assumed that these respective units preferably included in the control unit 110 are configured in the control unit 110 by the control unit 110 executing software that executes the processes illustrated in FIG. 19, mentioned later. However, the present invention is not limited thereto, and the respective units included in the control unit 110 may each be configured within the control unit 110 as hardware circuitry, for example.

Note also that it is assumed that the respective units included in the memory 120 preferably are temporarily configured in the memory 120 by the control unit 110 executing software for executing the processes illustrated in FIG. 19, mentioned later. However, the present invention is not limited thereto, and the respective units included in the memory 120 may each be configured as a dedicated storage device, for example.

In addition, the respective units included in the memory 120 may be temporarily configured in an internal memory of the control unit 110, such as a register, rather than being configured in the memory 120, for example.

The acceleration reading control unit 111 detects the accelerations Ax(t), Ay(t), and Az(t) in the three axial directions from the accelerometer 170.

Here, as described with reference to FIGS. 6A-6C, in the case where the three axial directions of the accelerometer match the directions of the X axis, Y axis, and Z axis, the detection values obtained by the accelerometer may be taken as-is as the acceleration data Ax(t), Ay(t), and Az(t) for the X axis, Y axis, and Z axis directions, respectively.

On the other hand, in the case where the three axial directions of the accelerometer do not match the directions of the X axis, Y axis, and Z axis, the detection values obtained by the accelerometer are converted into coordinates in order to calculate the acceleration data Ax(t), Ay(t), and Az(t) for the X axis, Y axis, and Z axis directions, respectively.

Then, the acceleration reading control unit 111 stores the acceleration data Ax(t), Ay(t), and Az(t), calculated for each of sampling cycles, in the acceleration data storage unit 121 of the memory 120.

Based on the acceleration data Ax(t), Ay(t), and Az(t) stored in the acceleration data storage unit 121, the characteristic point position specification unit 112 uses Formulas (1) through (9) to calculate the relative positions X(t), Y(t), and Z(t) that are relative to the average positions in the X axis, Y axis, and Z axis directions, respectively, in the short amount of time for the activity meter 100 (here, a time between ±1 steps (±T seconds)), as described with reference to FIGS. 6A-6C.

Figure 19A:
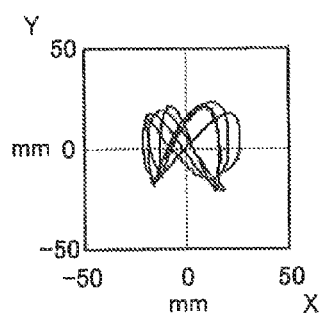
FIGS. 19A through 19C are first diagrams illustrating trajectories of a user's predetermined area calculated by the activity meter according to a preferred embodiment of the present invention.
Figure 19B:
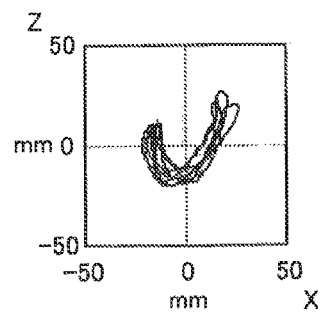
Figure 19C:
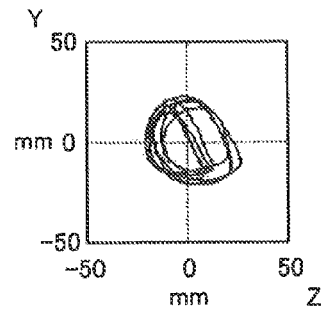
Figure 20A:
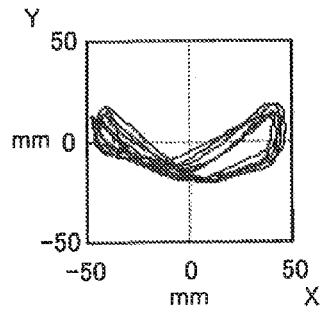
FIGS. 20A through 20C are second diagrams illustrating trajectories of a user's predetermined area calculated by the activity meter according to a preferred embodiment of the present invention.
Figure 20B:
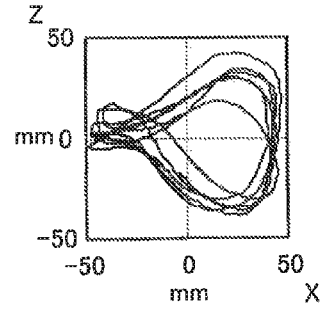
Figure 20C:
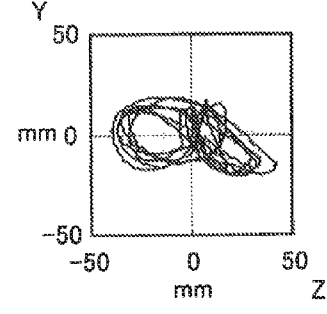

FIGS. 19A through 19C are first diagrams illustrating trajectories of a user's predetermined area calculated by the activity meter 100 according to this preferred embodiment. FIGS. 20A through 20C are second diagrams illustrating trajectories of the user's predetermined area calculated by the activity meter 100 according to this preferred embodiment.

The trajectories shown in FIGS. 19A through 19C are trajectories of the waist, which is the predetermined area, when the user is not fatigued. On the other hand, the trajectories shown in FIGS. 20A through 20C are trajectories of the waist, which is the predetermined area, when the user is fatigued. These trajectories are obtained by plotting the positions X(t), Y(t), and Z(t) calculated by the characteristic point position specification unit 112 on the XY plane, the XZ plane, and the YZ plane, respectively, while varying a time t.

In this manner, the amplitude from the center is greater, or in other words, the body axis moves more when the user is fatigued than when the user is not fatigued; in particular, in the trajectory in the XZ plane, there is a high level of variation in the trajectory from cycle to cycle.

Returning to FIG. 18, next, the characteristic point position specification unit 112 specifies coordinate values for the positions of the characteristic points through the method described with reference to FIGS. 7A through 9, based on the calculated positions X(t), Y(t), and Z(t). In other words, based on the accelerations detected by the accelerometer 170, the characteristic point position specification unit 112 specifies the positions of the characteristic points in the trajectories projected onto the XZ plane, the XY plane, and the YZ plane, which are planes perpendicular or substantially perpendicular to the three orthogonal axial directions, or the Y axis direction (the vertical direction), the Z axis direction (the direction in which the user advances), and the X axis direction (the horizontal direction), without the Z axis direction movement component.

Note that not all of the characteristic points need be specified, and only the characteristic points required for calculating the characteristic factors, described later, may be specified.

Next, the characteristic point position specification unit 112 stores the calculated positions of the characteristic points in the characteristic point position storage unit 122.

Based on the positions of the characteristic points stored in the characteristic point position storage unit 122, the characteristic factor calculation unit 1131 calculates the values of the characteristic factors in accordance with the calculation formulas described with reference to FIGS. 10A through 12B. Then, the characteristic factor calculation unit 1131 stores the calculated values of the characteristic factors in the characteristic factor storage unit 1231.

The multi regression formulas described with reference to the aforementioned FIGS. 13A through 16B are stored in advance in the correlation relationship storage unit 1232.

Based on the values of the characteristic factor stored in the characteristic factor storage unit 1231, the index calculation unit 1132 calculates indices indicating a gait posture (for example, the step size, the step spacing, waist rotation, foot lift height, back muscle extension, center of gravity balance, and so on), in accordance with the multi regression formulas stored in the correlation relationship storage unit 1232. Then, the index calculation unit 1132 stores the calculated values of the indices in the index storage unit 1233.

Figure 21:
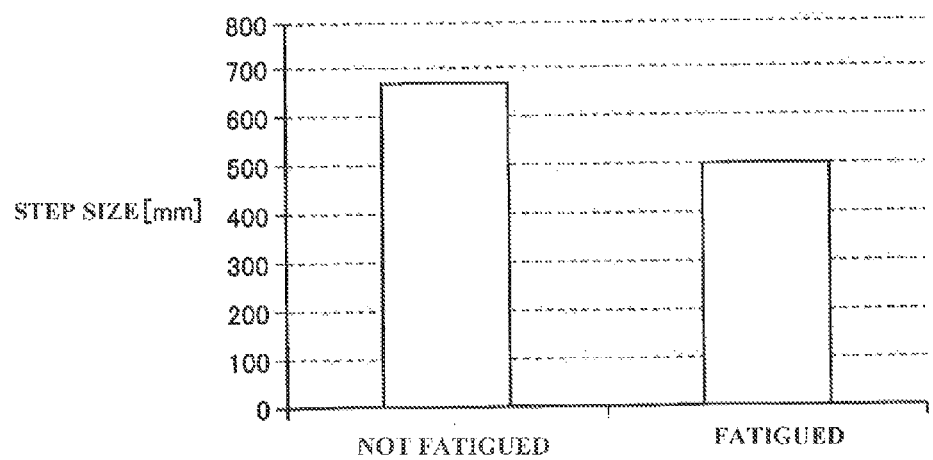
FIG. 21 is a graph illustrating a step size of a user calculated by the activity meter according to a preferred embodiment of the present invention.
Figure 22:
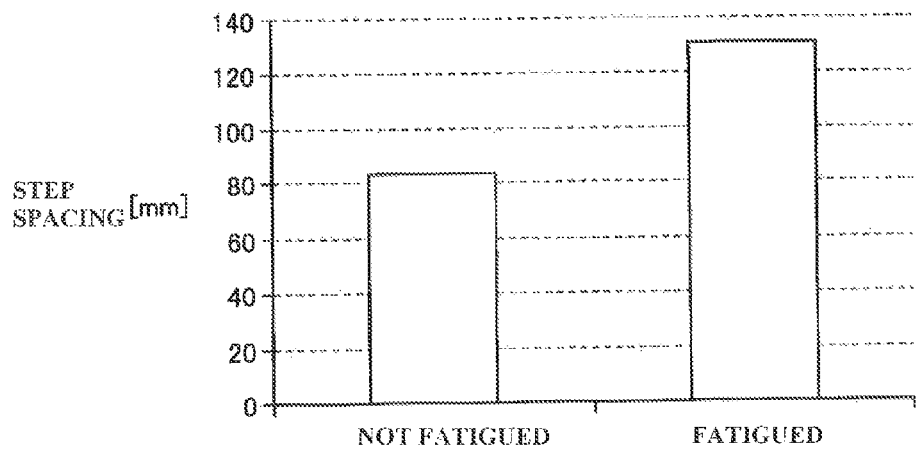
FIG. 22 is a graph illustrating a step spacing of a user calculated by the activity meter according to a preferred embodiment of the present invention.

FIG. 21 is a graph illustrating the step size of the user calculated by the activity meter 100 according to this preferred embodiment. FIG. 22 is a graph illustrating the step spacing of the user calculated by the activity meter 100 according to this preferred embodiment.

FIGS. 21 and 22 illustrate the user's step size and step spacing calculated based on the trajectories of the user's waist illustrated in FIGS. 19 and 20, respectively. These graphs both illustrate values when the user is not fatigued on the left side and when the user is fatigued on the right side.

As shown in FIG. 21, the step size when the user that is the target of measurement is not fatigued preferably is approximately 675 mm, whereas the step size when the user is fatigued preferably is approximately 500 mm, for example. As shown in FIG. 22, the step spacing when the user that is the target of measurement is not fatigued preferably is approximately 84 mm, whereas the step size when the user is fatigued preferably is approximately 130 mm, for example.

In this manner, the step size is smaller and the step spacing is greater when the user is fatigued than when the user is not fatigued.

Returning to FIG. 18, the gait posture determination unit 1133 determines a gait posture based on the values of the indices stored in the index storage unit 1233. The gait posture determination unit 1133 then stores the determined gait posture in the gait posture storage unit 1234 of the memory 120.

The temporal change amount calculation unit 1134 calculates a temporal change amount in the gait posture determined based on the index values and stored in the gait posture storage unit 1234, and stores the temporal change amount in the temporal change amount storage unit 1235 of the memory 120. For example, the degree to which an index indicating the gait posture, such as the step size and the step spacing, has changed since the exercise began is calculated. Alternatively, the degree to which a time derivative value indicating the gait posture has changed since the exercise began may be calculated.

The change degree determination unit 114 determines a degree of change, which is the degree of the temporal change, based on the temporal change amount calculated by the temporal change amount calculation unit 1134 and stored in the temporal change amount storage unit 1235, and stores that degree of change in the change degree storage unit 125 of the memory 120. In particular, in the present preferred embodiment, a posture change degree, which is a degree of temporal change in the gait posture, preferably is determined. However, the present invention is not limited thereto, and another degree of change, such as a degree of change in an index indicating the gait posture, may be used as long as it is a degree of the temporal change in the trajectory, for example.

The fatigue level input acceptance control unit 115 carries out control so as to accept, from the operation unit 130, the input of a level of fatigue when, for example, the user is moving. The level of fatigue whose input has been accepted is stored in the gait change-fatigue correspondence storage unit 124 of the memory 120 in association with the level of fatigue determined by the change degree determination unit 114 as cumulative data for determining levels of fatigue in the future.

Based on the level of fatigue and the degree of change stored in the gait change-fatigue correspondence storage unit 124, the fatigue level determination unit 116 determines the level of fatigue corresponding to the degree of change calculated by the change degree determination unit 114 and stored in the change degree storage unit 125. The following can be considered as non-limiting examples of methods for determining the level of fatigue.

(1) The step size, gait pitch, and foot lift height at the start of exercise are taken as Sw0, Sp0, and Sh0, respectively, and the present step size, gait pitch, and foot lift height are taken as Swt, Spt, and Sht, respectively; the change amounts in each are taken as $\Delta Sw=Swt-Sw0$, $\Delta Sp=Spt-Sp0$, and $\Delta Sh=Sht-Sh0$, respectively. Note that other gait posture indices, such as the step spacing, the back muscle extension, the center of gravity balance, and the waist rotation, may be used as well, for example.

Then, as a result of a correspondence relationship between the level of fatigue and the degrees of change in the change amounts $\Delta Sw$, $\Delta Sp$, and $\Delta Sh$ being accumulated in the memory 120 (the gait change-fatigue correspondence storage unit 124), thresholds $\Delta Swth$, $\Delta Spth$, and $\Delta Shth$ are set for the respective change amounts $\Delta Sw$, $\Delta Sp$, and $\Delta Sh$.

For example, from the data stored in the gait change-fatigue correspondence storage unit 124, intermediate values between an average value when the user is fatigued and an average value when the user is not fatigued are set as the thresholds $\Delta Swth$, $\Delta Spth$, and $\Delta Shth$ for the change amounts $\Delta Sw$, $\Delta Sp$, and $\Delta Sh$, respectively.

The fatigue level determination unit 116 determines that a first stage for the level of fatigue has been reached when one of the change amounts $\Delta Sw$, $\Delta Sp$, and $\Delta Sh$ is below its threshold, a second stage for the level of fatigue has been reached when two of the change amounts $\Delta Sw$, $\Delta Sp$, and $\Delta Sh$ are below their thresholds, and a third stage for the level of fatigue has been reached when all of the change amounts $\Delta Sw$, $\Delta Sp$, and $\Delta Sh$ are below their thresholds.

Note that instead, the level of fatigue may be determined to have returned to the second stage for the level of fatigue when during the third stage for the level of fatigue one of the change amounts $\Delta Sw$, $\Delta Sp$, and $\Delta Sh$ is greater than or equal to its threshold, may be determined to have returned to the first stage for the level of fatigue when during the second stage for the level of fatigue two of the change amounts $\Delta Sw$, $\Delta Sp$, and $\Delta Sh$ is greater than or equal to its threshold, and may be determined to have returned completely when during the first stage for the level of fatigue all of the change amounts $\Delta Sw$, $\Delta Sp$, and $\Delta Sh$ are greater than or equal to their thresholds.

The thresholds when determining that the level of fatigue has returned completely may be set to stricter conditions than for the thresholds when determining that the level of fatigue has increased (that is, the thresholds $\Delta Swth$, $\Delta Spth$, and $\Delta Shth$ are increased for the step size, the gait pitch, and the foot lift height). Through this, a mistaken determination that the user is no longer fatigued even though the user is actually fatigued can be prevented, thus preventing damage the user, which in turn makes it possible to ensure the safety of the user.

(2) In the aforementioned non-limiting example (1), the step size Sw0, gait pitch Sp0, and foot lift height Sh0 at the start of walking preferably are taken as initial values. However, the present invention is not limited thereto, and average values over a predetermined amount of time (for example, two hours) following the start of exercise may be taken as the initial values, for example.

(3) In the aforementioned non-limiting example (1), the level of fatigue is preferably determined based on a relationship between change amounts, which are differences between present values and initial values, and thresholds. However, the present invention is not limited thereto, and the level of fatigue may be determined based on a relationship between a percentage of change from the initial values to the present values and thresholds, for example.

(4) In the aforementioned non-limiting example (1), the stage of the level of fatigue preferably is raised when a threshold is exceeded. However, the present invention is not limited thereto, and the stage of the level of fatigue may be raised in the case where a state in which the threshold is exceeded continues for a set amount of time (for example, one minute), for example.

(5) In the aforementioned non-limiting example (1), each time the type of exercise (for example, running and walking) changes, the initial values may be changed to initial values that are based on the type of exercise, for example. Doing so makes it possible to determine the level of fatigue and accurate manner even for exercise in which running and walking are alternated every several minutes.

(6) In the aforementioned non-limiting example (1), it may be determined that the user has recovered from his/her fatigue in the case where there is no exercise for a predetermined amount of time (for example, one hour or more), and the initial values may be reset, for example.

(7) Variations in the step size, gait pitch, and foot lift height during a predetermined amount of time (for example, one minute) are taken as $\sigma w$, $\sigma p$, and $\sigma h$, respectively. Then, as a result of a correspondence relationship between the level of fatigue and the degrees of change in the variations $\sigma w$, $\sigma p$, and $\sigma h$ being accumulated in the memory 120 (the gait change-fatigue correspondence storage unit 124), thresholds $\sigma wth$, $\sigma pth$, and $\sigma hth$ are set for the respective variations $\sigma w$, $\sigma p$, and $\sigma h$.

The fatigue level determination unit 116 determines that a first stage for the level of fatigue has been reached when one of the variations $\sigma w$, $\sigma p$, and $\sigma h$ is below its threshold, a second stage for the level of fatigue has been reached when two of the variations $\sigma w$, $\sigma p$, and $\sigma h$ are below their thresholds, and a third stage for the level of fatigue has been reached when all of the variations $\sigma w$, $\sigma p$, and $\sigma h$ are below their thresholds.

(8) Time derivative values for the present step size Swt, gait pitch Spt, and foot lift height Sht are taken as $Swt'=dSwt/dt$, $Spt'=dSpt/dt$, and $Sht'=dSht/dt$, respectively. Then, as a result of a correspondence relationship between the level of fatigue and the time derivative values $Swt'$, $Spt'$, and $Sht'$ being accumulated in the memory 120 (the gait change-fatigue correspondence storage unit 124), thresholds are set for the respective time derivative values $Swt'$, $Spt'$, and $Sht'$.

The fatigue level determination unit 116 determines that a first stage for the level of fatigue has been reached when one of the time derivative values $Swt'$, $Spt'$, and $Sht'$ is below its threshold, a second stage for the level of fatigue has been reached when two of the time derivative values $Swt'$, $Spt'$, and $Sht'$ are below their thresholds, and a third stage for the level of fatigue has been reached when all of the time derivative values $Swt'$, $Spt'$, and $Sht'$ are below their thresholds.

The alert control unit 117 carries out control that alerts the user of the level of fatigue determined by the fatigue level determination unit 116. As a method for performing the alert, the display unit 140 may be controlled to carry out the display, the audio alert unit 150 may be controlled to output audio, or a combination of a display and audio output may be carried out, for example.

As the display, the level of fatigue may be displayed as an icon, or may be displayed as text, for example. As the audio output, a buzzer sound may be outputted at a volume that is based on the level of fatigue, a buzzer sound may be outputted at an interval that is based on the level of fatigue, a buzzer sound may be outputted using a different sound based on the level of fatigue, or a word expressing the level of fatigue may be outputted, for example. Because the audio may sound different to the user depending on his/her level of fatigue, it is desirable to output the audio at a volume and using a sound that is easy to hear in accordance with the level of fatigue.

Figure 23:
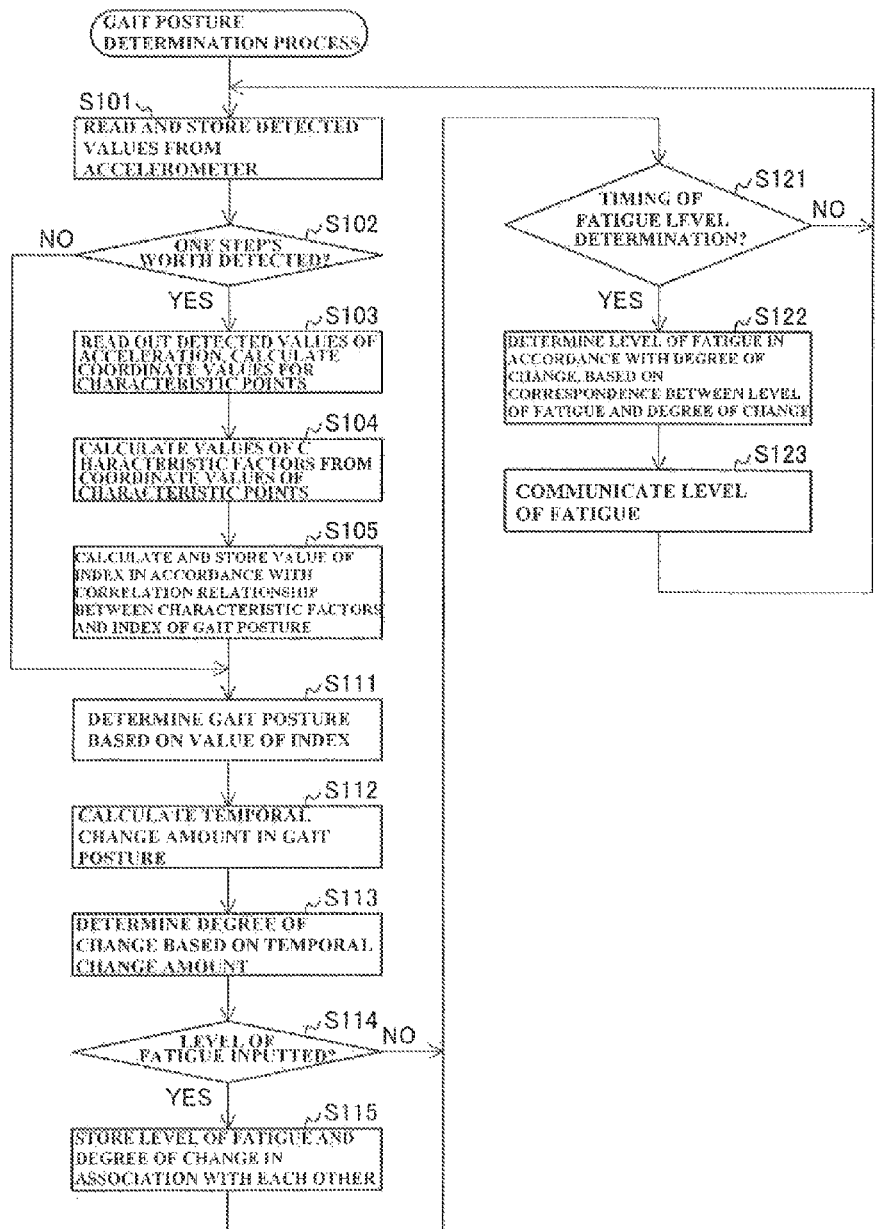
FIG. 23 is a flowchart illustrating the flow of a gait posture determination process executed by a control unit of the activity meter according to a preferred embodiment of the present invention.

FIG. 23 is a flowchart illustrating the flow of a gait posture determination process executed by the control unit 110 of the activity meter 100 according to this preferred embodiment. As shown in FIG. 23, in step S101, the control unit 110 reads the accelerometer detection values from the accelerometer 170 and stores the acceleration data Ax(t), Ay(t), and Az(t) in the memory 120 for each of the sampling cycles, as mentioned in the descriptions of the acceleration reading control unit 111 made with reference to FIG. 18.

Next, in step S102, the control unit 110 determines whether or not one step's worth of walking has been detected. Here, it is determined that one step's worth of walking has been detected when the characteristic point (1) (the characteristic point (5)) illustrated in FIGS. 7A and 7B has been detected. In the case where it has been determined that one step's worth of walking has not been detected (that is, in the case where a determination of NO has been made in step S102), the control unit 110 advances the processing being executed to the process in step S111.

On the other hand, in the case where it has been determined that one step's worth of walking has been detected (that is, in the case where a determination of YES has been made in step S102), in step S103, the control unit 110 reads out one step's worth of the acceleration data Ax(t), Ay(t), and Az(t) stored in the memory 120 in step S101, and calculates the coordinate values of the positions of the characteristic points, as mentioned in the descriptions of the characteristic point position specification unit 112 made with reference to FIG. 18.

Next, in step S104, the control unit 110 calculates the values of the characteristic factors based on the coordinate values of the positions of the characteristic points calculated in step S103, as mentioned in the descriptions of the characteristic factor calculation unit 1131 made with reference to FIG. 18.

Next, in step S105, based on the values of the characteristic factors calculated in step S104, the control unit 110 calculates values of the gait posture indices in accordance with the correlation relationships between the characteristic factors and the indices and stores the calculated values in the memory 120, as mentioned in the descriptions of the index calculation unit 1132 made with reference to FIG. 18. Thereafter, the control unit 110 advances the processing being executed to the process in step S111.

In step S111, the control unit 110 reads out the indices indicating the gait posture stored in the memory 120 in step S105, and based on those indices, determines the gait posture and stores the gait posture in the memory 120, as mentioned in the descriptions of the gait posture determination unit 1133 made with reference to FIG. 18.

Next, in step S112, the control unit 110 calculates the temporal change amount of the gait posture determined in step S111 and stores that temporal change amount in the memory 120, as mentioned in the descriptions of the temporal change amount calculation unit 1134 made with reference to FIG. 18.

Next, in step S113, the control unit 110 determines the degree of change, which is the degree of temporal change, and stores that degree of change in the memory 120, as mentioned in the descriptions of the change degree determination unit 114 made with reference to FIG. 18.

Then, in step S114, the control unit 110 determines whether or not an input of the level of fatigue has been accepted through the operation unit 130. In the case where it is determined that such an input has been accepted (that is, in the case where a determination of YES has been made in step S114), in step S115, the control unit 110 associates the level of fatigue whose input has been accepted with the level of fatigue calculated in step S113 and stores the associated data in the memory 120, as mentioned in the descriptions of the fatigue level input acceptance control unit 115 made with reference to FIG. 18.

In the case where it has been determined that an input of the level of fatigue has not been accepted (that is, the case where a determination of NO has been made in step S114), and after step S115, the control unit 110 determines, in step S121, whether or not a timing for determining the level of fatigue (for example, a timing occurring every minute) has been reached. In the case where it has been determined that the timing has not been reached (that is, in the case where a determination of NO has been made in step S121), the control unit 110 returns the processing being executed to the process in step S101.

On the other hand, in the case where it has been determined that the timing to determine the level of fatigue has been reached (that is, the case where a determination of YES has been made in step S121), in step S122, the control unit 110 determines the level of fatigue corresponding to the degree of change calculated in step S113 based on the levels of fatigue and degrees of change stored in the memory 120, as mentioned in the descriptions of the fatigue level determination unit 116 made with reference to FIG. 18.

Next, in step S123, the control unit 110 performs control so as to alert the user of the level of fatigue determined in step S122, as mentioned in the descriptions of the alert control unit 117 made with reference to FIG. 18. Thereafter, the control unit 110 returns the processing being executed to the process in step S101.

As described above, the activity meter 100 according to the present preferred embodiment preferably includes the main body unit 191, the accelerometer 170, and the control unit 110, and is a device for determining the gait posture of the user who wears the main body unit 191 on his/her waist.

The control unit includes the characteristic point position specification unit 112 that, based on the accelerations detected by the accelerometer 170, specifies a trajectory of the waist of the user who is wearing the main body unit 191 during walking; a temporal change calculation unit (this includes the characteristic factor calculation unit 1131, the index calculation unit 1132, the gait posture determination unit 1133, and the temporal change amount calculation unit 1134) that calculates a temporal change in the trajectory specified by the characteristic point position specification unit 112; and the change degree determination unit 114 (this includes the fatigue level input acceptance control unit 115 and the fatigue level determination unit 116) that determines, based on the temporal change calculated by the temporal change calculation unit, a degree of change that is a degree of the temporal change.

Accordingly, the degree of the temporal change in the trajectory of the user's waist is determined, making the device less susceptible to the influence of the user simply changing his/her movement speed or the influence of differences among individual users. As a result, the user can be alerted of the degree of change in his/her gait in a more accurate manner.

In addition, the activity meter 100 further includes the memory 120. The control unit 110 further includes the fatigue level input acceptance control unit 115 that accepts an input of the level of fatigue when the user is walking. The change degree determination unit 114 calculates the degree of change when the input of the level of fatigue has been accepted by the fatigue level input acceptance control unit 115. The fatigue level input acceptance control unit 115 stores the level of fatigue that has been accepted in the gait change-fatigue correspondence storage unit 124 of the memory 120 in association with the level of fatigue determined by the change degree determination unit 114. The control unit 110 further includes the fatigue level determination unit 116 that, based on the level of fatigue and the degree of change stored in the gait change-fatigue correspondence storage unit 124, determines the level of fatigue corresponding to the degree of change determined by the change degree determination unit 114. The alert control unit 117 alerts the user of the level of fatigue determined by the fatigue level determination unit 116 using the display unit 140 or the audio alert unit 150.

In addition, the activity meter 100 further includes the display unit 140 or the audio alert unit 150. The control unit 110 further includes the alert control unit 117 that alerts the user of the level of fatigue determined by the fatigue level determination unit 116 using the display unit 140 or the audio alert unit 150.

The trajectory is a three-dimensional trajectory from which a movement component in the direction in which the waist on which the main body unit 191 is worn advances (that is, the Z axis direction) has been removed. The trajectory has the patterns described in FIGS. 7A through 9. The pattern includes multiple characteristic points that define a characteristic of the pattern.

Based on the accelerations detected by the accelerometer 170, the characteristic point position specification unit 112 specifies the positions of the characteristic points in the trajectory, from which the movement component in the direction of advancement (that is, the Z axis direction) has been removed, projected onto the XZ plane, the XY plane, and the YZ plane, which are planes that are perpendicular or substantially perpendicular to the vertical direction (Y axis direction), the direction of advancement (the Z axis direction), and the horizontal direction (the X axis direction), respectively. The characteristic factor calculation unit 1131 calculates values of characteristic factors in the trajectory based on the positions specified by the characteristic point position specification unit 112. Based on the values of the characteristic factors calculated by the characteristic factor calculation unit 1131, the index calculation unit 1132 calculates values of indices indicating a gait posture in accordance with a predetermined correlation relationship between the values of the characteristic factors and the values of the indices. The temporal change amount calculation unit 1134 calculates a temporal change amount in the indices based on the values of the indices calculated by the index calculation unit 1132. The change degree determination unit 114 determines a degree of change based on the temporal change amount calculated by the temporal change amount calculation unit 1134.

Accordingly, the indices indicating the gait are calculated accurately based on an accurate correlation relationship, and indices indicating various gaits are calculated, making it possible to determine a detailed degree of change in a more accurate manner.

The temporal change amount may further include a temporal change amount of the gait posture. The control unit 110 may further include the gait posture determination unit 1133 that determines the gait posture based on the values of the indices calculated by the index calculation unit 1132. The temporal change amount calculation unit 1134 calculates a temporal change amount in the gait posture determined by the gait posture determination unit 1133. The change degree determination unit 114 determines a degree of change, including the posture change degree in the temporal change of the gait posture, based on the temporal change amount calculated by the temporal change amount calculation unit 1134.

Accordingly, the indices indicating the gait posture are calculated accurately based on an accurate correlation relationship, and indices indicating various gait posture's are calculated, making it possible to determine a detailed degree of change in a more accurate manner.

In addition, as described with reference to FIGS. 13A through 16B, the correlation relationship is indicated by a multi regression formula, which is a relational expression between the value of the characteristic factor serving as a response variable and the value of the index serving as an explaining variable, obtained through a multi regression analysis.

Furthermore, the characteristic points include the characteristic point (1) when the right foot touches the ground and the characteristic point (2) when the trajectory reaches the highest position while the user is standing on his/her right foot, as well as the characteristic point (3) when the left foot touches the ground and the characteristic point (4) when the trajectory reaches the highest position while the user is standing on his/her left foot.

The characteristic factors include the characteristic factor Hr, which is a distance between the characteristic point (1) and the characteristic point (2) in the vertical direction (the Y axis direction) in the trajectory projected onto the XY plane that is perpendicular or substantially perpendicular to the direction of advancement (the Z axis direction), and the characteristic factor StShi, which is calculated from a distance between the characteristic point (1) and the characteristic point (2) and the distance between the characteristic point (3) and the characteristic point (4) in the trajectory projected onto the YZ plane that is perpendicular or substantially perpendicular to the horizontal direction (the X axis direction).

The indices include the step size. The multi regression formula is "step size Length=$\alpha \times$Hr+$\beta \times$StShi+$\gamma$", that calculates the sum of the product of the partial regression coefficient $\alpha$ obtained through the multi regression analysis and the characteristic factor Hr, the product of the partial regression coefficient $\beta$ obtained through the multi regression analysis and the characteristic factor StShi, and the partial regression coefficient $\gamma$.

Furthermore, the characteristic points include the characteristic point (1) when the right foot touches the ground, the characteristic point (2) when the trajectory reaches the highest position while the user is standing on his/her right foot, the characteristic point (6) furthest to the right in the trajectory, and the characteristic point (7) furthest to the left in the trajectory, as well as the characteristic point (10) furthest forward on the right side in the trajectory, the characteristic point (12) furthest forward on the left side in the trajectory, the characteristic point (9) furthest rearward on the right side in the trajectory, and the characteristic point (11) furthest rearward on the left side in the trajectory.

The characteristic factors preferably include the characteristic factor Hr/W, which is the quotient obtained by dividing a distance Hr between the characteristic point (1) and the characteristic point (2) in the vertical direction (the Y axis direction) in the trajectory projected onto the XY plane that is perpendicular or substantially perpendicular to the direction of advancement (the Z axis direction), by a distance W between the characteristic point (6) and the characteristic point (7) in the horizontal direction (the X axis direction); and the characteristic factor WuSu/WdSu, which is the quotient obtained by dividing a distance WuSu between the characteristic point (10) and the characteristic point (12) in the horizontal direction (the X axis direction) in the trajectory projected onto the XZ plane that is perpendicular or substantially perpendicular to the vertical direction (the Y axis direction), by a distance WdSu between the characteristic point (9) and the characteristic point (11) in the horizontal direction (the X axis direction).

The indices include the step spacing. The multi regression formula is "step spacing Width=δ×Hr/W+ε×WuSu/WdSu+ζ", that calculates the sum of the product of the partial regression coefficient δ obtained through the multi regression analysis and the characteristic factor Hr/W, the product of the partial regression coefficient ε obtained through the multi regression analysis and the characteristic factor WuSu/WdSu, and the partial regression coefficient ζ.

Next, variations on the aforementioned preferred embodiment will be described.

In the aforementioned preferred embodiment, the posture change degree, which is the degree of temporal change in the gait posture, preferably is calculated based on the temporal change amount of the gait posture. However, the present invention is not limited thereto, and the degree of change, which is the degree of temporal change in the gait, may be calculated based on the temporal change amount of an index indicating the gait, for example. Alternatively, the degree of change may be calculated based on temporal changes in the trajectory of the user's waist, for example.

In the aforementioned preferred embodiment, the correspondence relationship between the level of fatigue and the degree of change preferably is set as a result of the user inputting the level of fatigue. However, the present invention is not limited thereto, and data of the correspondence relationship between the level of fatigue and the degree of change may be obtained in the same manner for multiple users, and the obtained correspondence relationships may be stored in the memory 120 of the activity meter 100 (that is, the gait change-fatigue correspondence storage unit 124) in advance, for example. By doing so, data of the correspondence relationship between the level of fatigue and the degree of change need not be accumulated by accepting the user's input of the level of fatigue, making it possible to avoid burdening the user.

In the aforementioned preferred embodiment, the gait posture preferably is determined based on a relationship between the values of indices and thresholds. However, the present invention is not limited thereto, in the gait posture may be determined based on a degree of resemblance between a set of indices for which the relationship with the gait posture has been found in advance and a set of calculated indices, for example.

The thresholds for the indices indicating the gait posture may be determined based on data actually measured by having a user with a good gait posture walk, for example.

In the aforementioned preferred embodiment, as described with reference to FIG. 21, a target gait posture and the user's gait posture preferably are displayed separately. However, the present invention is not limited thereto, and the target gait posture and the user's gait posture may be displayed in an overlapping manner, for example.

In the aforementioned preferred embodiment, an average velocity component preferably is an average velocity component for ±one step's worth of time, as illustrated in Formulas 4 through 6. However, the present invention is not limited thereto, and the average velocity component may be an average velocity component for ±n steps' worth of time (where n is a predetermined number), an average velocity component for −n steps' worth of time (that is, n steps prior to a time when the calculation is to be performed), an average velocity component for ±s second (where s is a predetermined number), or an average velocity component for −s seconds' (that is, n seconds prior to when the calculation is to be performed), for example.

The aforementioned preferred embodiment describes the activity meter 100 as an apparatus. However, the present invention is not limited thereto, and can also be a control method for controlling the activity meter 100, for example.

Note that the preferred embodiment disclosed above is to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

The invention claimed is:

1. A gait change determination device comprising:
   a main body arranged to be worn by a user in a predetermined area;
   an accelerometer that detects an acceleration of the main body; and
   a control unit that is arranged and programmed to determine a change in a gait of the user; wherein
   the control unit includes:
      a specification unit that is arranged and programmed to, based on the acceleration detected by the accelerometer, specify a trajectory of the predetermined area on which the main body is worn during walking;
      a first calculation unit that is arranged and programmed to calculate a temporal change in the trajectory specified by the specification unit; and
      a determination unit that is arranged and programmed to, based on the temporal change calculated by the first calculation unit, determine a degree of change that is the degree of the temporal change.

2. The gait change determination device according to claim 1, wherein
   the control unit includes an acceptance unit that is arranged and programmed to accept an input of a level of fatigue when the user is walking;
   the determination unit is arranged and programmed to determine the degree of change when the degree of change has been accepted by the acceptance unit;
   the control unit further includes a storage unit that is arranged and programmed to store the level of fatigue accepted by the acceptance unit and the degree of change determined by the determination unit in association with each other in the storage unit; and
   the determination unit is arranged and programmed to determine the level of fatigue that corresponds to the degree of change determined by the determination unit based on the level of fatigue and the degree of change stored in the storage unit.

3. The gait change determination device according to claim 2, further comprising an alert unit, wherein the control unit includes an alert control unit that is arranged and programmed to communicate the level of fatigue determined by the determination unit using the alert unit.

4. The gait change determination device according to claim 1, wherein
   the trajectory is a three-dimensional trajectory from which a movement component in an advancement direction in which the predetermined area on which the main body is worn advances during walking has been removed, and a pattern of the trajectory includes a plurality of characteristic points that define characteristics of the pattern;

the specification unit is arranged and programmed to specify positions of the characteristic points in the trajectory projected, with the movement component in the advancement direction removed, onto planes perpendicular to each of three axial directions, including a vertical direction, the advancement direction, and a horizontal direction, based on the acceleration calculated by the accelerometer;

the first calculation unit includes:
  a second calculation unit that is arranged and programmed to calculate values of characteristic factors of the trajectory based on the positions specified by the specification unit;
  a third calculation unit that is arranged and programmed to, in accordance with a correlation relationship, determined in advance, between the values of the characteristic factors and the value of an index indicating the gait, calculate a value of the index, based on the values of the characteristic factors calculated by the second calculation unit; and
  a fourth calculation unit that is arranged and programmed to calculate a temporal change amount of the index based on the value of the index calculated by the third calculation unit; and the determination unit is arranged and programmed to determine the degree of change based on the temporal change amount calculated by the fourth calculation unit.

5. The gait change determination device according to claim 4, wherein
the temporal change amount includes a temporal change amount of a gait posture;
the control unit includes a gait posture determination unit that determines the gait posture based on the value of the index calculated by the third calculation unit;
the fourth calculation unit is arranged and programmed to calculate the temporal change amount of the gait posture determined by the gait posture determination unit; and
the determination unit is arranged and programmed to determine the degree of change, including a posture change degree in the temporal change of the gait posture, based on the temporal change amount calculated by the fourth calculation unit.

6. The gait change determination device according to claim 4, wherein the correlation relationship is indicated by a multi regression formula that is a relational expression between the values of the characteristic factors serving as a response variable and the value of the index serving as an explaining variable, obtained through a multi regression analysis.

7. The gait change determination device according to claim 6,
wherein the characteristic points include a first characteristic point when a first foot touches the ground, a second characteristic point when the trajectory reaches the highest position while the user is standing on the first foot, a third characteristic point when a second foot touches the ground, and a fourth characteristic point when the trajectory reaches the highest position while the user is standing on the second foot;

the characteristic factors include a first characteristic factor that is a distance between the first characteristic point and the second characteristic point in the vertical direction in the trajectory projected onto the plane that is perpendicular to the advancement direction, and a second characteristic factor that is calculated from a distance between the first characteristic point and the second characteristic point and a distance between the third characteristic point and the fourth characteristic point in the trajectory projected onto the plane that is perpendicular to the horizontal direction;

the index includes a step size; and the multi regression formula is a formula (Length=$\alpha \times$Hr+$\beta \times$StShi+$\gamma$) that calculates the sum of the product of a first partial regression coefficient ($\alpha$) obtained through the multi regression analysis and the first characteristic factor, the product of a second partial regression coefficient ($\beta$) obtained through the multi regression analysis and the second characteristic factor, and a third partial regression coefficient ($\gamma$).

8. The gait change determination device according to claim 6, wherein the characteristic points include a first characteristic point when a first foot touches the ground, a second characteristic point when the trajectory reaches the highest position while the user is standing on the first foot, a third characteristic point furthest to the right in the trajectory, a fourth characteristic point furthest to the left in the trajectory, a fifth characteristic point furthest forward on the right side in the trajectory, a sixth characteristic point furthest forward on the left side in the trajectory, a seventh characteristic point furthest rearward on the right side in the trajectory, and an eighth characteristic point furthest rearward on the left side in the trajectory;

the characteristic factors include a first characteristic factor that is a quotient obtained by dividing a distance between the first characteristic point and the second characteristic point in the vertical direction in the trajectory projected onto the plane that is perpendicular to the advancement direction, by a distance between the third characteristic point and the fourth characteristic point in the horizontal direction, and a second characteristic factor that is a quotient obtained by dividing a distance between the fifth characteristic point and the sixth characteristic point in the horizontal direction in the trajectory projected onto the plane that is perpendicular to the vertical direction, by a distance between the seventh characteristic point and the eighth characteristic point in the horizontal direction;

the index includes a step spacing; and the multi regression formula is a formula (Width=$\delta \times$Hr/W+$\epsilon \times$WuSu/WdSu+$\zeta$) that calculates the sum of the product of a first partial regression coefficient ($\delta$) obtained through the multi regression analysis and the first characteristic factor, the product of a second partial regression coefficient ($\epsilon$) obtained through the multi regression analysis and the second characteristic factor, and a third partial regression coefficient ($\zeta$).

* * * * *